(12) United States Patent
Ng et al.

(10) Patent No.: US 11,076,865 B2
(45) Date of Patent: Aug. 3, 2021

(54) KNOTLESS FILAMENT ANCHOR FOR SOFT TISSUE REPAIR

(71) Applicant: Howmedica Osteonics Corp., Mahwah, NJ (US)

(72) Inventors: Tracy Pat-Yen Ng, Denver, CO (US); Kyle Craig Pilgeram, San Jose, CA (US); Lee Harris Cordova, Denver, CO (US); Robert Eugene McLaughlin, II, Manchester, MA (US); Stuart Edward Fromm, Rapid City, SD (US)

(73) Assignee: Howmedica Osteonics Corp., Mahwah, NJ (US)

( * ) Notice: Subject to any disclaimer, the term of this patent is extended or adjusted under 35 U.S.C. 154(b) by 553 days.

(21) Appl. No.: 15/878,026

(22) Filed: Jan. 23, 2018

(65) Prior Publication Data

US 2018/0146961 A1    May 31, 2018

Related U.S. Application Data

(60) Division of application No. 14/308,208, filed on Jun. 18, 2014, now abandoned, which is a continuation of
(Continued)

(51) Int. Cl.
*A61B 17/16* (2006.01)
*A61B 17/04* (2006.01)
(Continued)

(52) U.S. Cl.
CPC ...... *A61B 17/1615* (2013.01); *A61B 17/0401* (2013.01); *A61B 17/06166* (2013.01);
(Continued)

(58) Field of Classification Search
CPC .......... A61B 17/0401; A61B 17/06166; A61B 2017/0414; A61B 2017/0409; A61B 2017/0427; A61B 17/1615
See application file for complete search history.

(56) References Cited

U.S. PATENT DOCUMENTS

| 749,624 A | 1/1904 | McCullough |
| 1,308,798 A | 7/1919 | Masland |

(Continued)

FOREIGN PATENT DOCUMENTS

| DE | 3131496 A1 | 2/1983 |
| DE | 4231101 A1 | 3/1994 |

(Continued)

OTHER PUBLICATIONS

Australian Examination Report for Application No. 2013202699 dated Feb. 21, 2014.
(Continued)

*Primary Examiner* — Sarah A Simpson
(74) *Attorney, Agent, or Firm* — Lerner, David, Littenberg, Krumholz & Mentlik, LLP

(57) ABSTRACT

In one embodiment, the present invention includes a method for securing tissue to bone, including drilling a bone hole into the bone; passing a filament through the tissue, the filament including a first end, a second end and a length therebetween, the second end having a loop; passing the first end of the filament through the loop of the filament; pulling on the first end of the filament such that the loop travels along the length of the filament and to the tissue; passing an anchor along the length of the filament, from the first end towards the loop and tissue; engaging the loop with a distal end of the anchor; positioning the distal end of the anchor, with the loop of the filament, into the bone hole; and securing the anchor in the bone.

19 Claims, 16 Drawing Sheets

Related U.S. Application Data application No. 13/441,290, filed on Apr. 6, 2012, now Pat. No. 9,808,242.

(51) Int. Cl.
  *A61B 17/06* (2006.01)
  *A61B 90/00* (2016.01)
(52) U.S. Cl.
  CPC ............... *A61B 2017/0403* (2013.01); *A61B 2017/0409* (2013.01); *A61B 2017/0427* (2013.01); *A61B 2090/0807* (2016.02)

(56) References Cited

U.S. PATENT DOCUMENTS

| | | |
|---|---|---|
| 2,250,434 A | 7/1941 | Dugaw |
| 2,267,925 A | 12/1941 | Johnston |
| 2,382,019 A | 8/1945 | Miller |
| 2,461,947 A | 2/1949 | Weber |
| 2,494,229 A | 1/1950 | Collison |
| 2,773,672 A | 12/1956 | Holmes et al. |
| 3,384,085 A | 5/1968 | Hall |
| 3,407,889 A | 10/1968 | Hjalsten et al. |
| 3,461,875 A | 8/1969 | Hall |
| 3,554,192 A | 1/1971 | Isbemer |
| 3,845,772 A | 11/1974 | Smith |
| 4,212,569 A | 7/1980 | Andersson et al. |
| 4,541,423 A | 9/1985 | Barber |
| 4,594,033 A | 6/1986 | Peetz et al. |
| 4,605,347 A | 8/1986 | Jodock et al. |
| 4,635,738 A | 1/1987 | Schillinger et al. |
| 4,706,659 A | 11/1987 | Matthews et al. |
| 4,728,231 A | 3/1988 | Kunimori et al. |
| 4,751,922 A | 6/1988 | DiPietropolo |
| 4,842,451 A | 6/1989 | Dugger |
| 5,007,911 A | 4/1991 | Baker |
| 5,122,134 A | 6/1992 | Borzone et al. |
| 5,141,520 A | 8/1992 | Goble et al. |
| 5,165,494 A | 11/1992 | Barr |
| 5,176,682 A | 1/1993 | Chow |
| 5,186,268 A | 2/1993 | Clegg |
| 5,190,548 A | 3/1993 | Davis |
| 5,259,846 A | 11/1993 | Granger et al. |
| 5,273,380 A | 12/1993 | Musacchia |
| RE34,762 E | 10/1994 | Goble et al. |
| 5,374,269 A | 12/1994 | Rosenberg |
| 5,380,334 A | 1/1995 | Torrie et al. |
| RE34,871 E | 3/1995 | McGuire et al. |
| 5,417,691 A | 5/1995 | Hayhurst |
| 5,423,824 A | 6/1995 | Akerfeldt et al. |
| 5,437,675 A | 8/1995 | Wilson |
| 5,496,348 A | 3/1996 | Bonutti |
| 5,505,736 A | 4/1996 | Reimels et al. |
| 5,522,844 A | 6/1996 | Johnson |
| 5,522,846 A | 6/1996 | Bonutti |
| 5,527,343 A | 6/1996 | Bonutti |
| 5,540,703 A | 7/1996 | Barker, Jr. et al. |
| 5,569,306 A | 10/1996 | Thal |
| 5,575,819 A | 11/1996 | Amis |
| 5,584,617 A | 12/1996 | Houser |
| 5,584,835 A | 12/1996 | Greenfield |
| 5,601,557 A | 2/1997 | Hayhurst |
| 5,647,874 A | 7/1997 | Hayhurst |
| 5,664,914 A | 9/1997 | Taniguchi |
| 5,681,315 A | 10/1997 | Szabo |
| 5,683,419 A | 11/1997 | Thal |
| 5,690,676 A | 11/1997 | DiPoto et al. |
| 5,699,657 A | 12/1997 | Paulson |
| 5,702,397 A | 12/1997 | Goble et al. |
| 5,707,374 A | 1/1998 | Schmidt |
| 5,709,708 A | 1/1998 | Thal |
| 5,713,905 A | 2/1998 | Goble et al. |
| 5,725,530 A | 3/1998 | Popken |
| 5,725,541 A | 3/1998 | Anspach, III et al. |
| 5,732,606 A | 3/1998 | Chiang |
| 5,733,307 A | 3/1998 | Dinsdale |
| 5,759,185 A * | 6/1998 | Grinberg ............ A61B 17/1615 606/180 |
| 5,782,864 A | 7/1998 | Lizardi |
| 5,782,866 A | 7/1998 | Wenstrom, Jr. |
| 5,788,699 A | 8/1998 | Bobst et al. |
| 5,885,294 A | 3/1999 | Pedlick et al. |
| 5,895,179 A | 4/1999 | Gschwend et al. |
| 5,908,423 A | 6/1999 | Kashuba et al. |
| 5,941,139 A | 8/1999 | Vodehnal |
| 5,941,883 A | 8/1999 | Sklar |
| 5,947,659 A | 9/1999 | Mays |
| 5,970,697 A | 10/1999 | Jacobs et al. |
| 5,980,558 A | 11/1999 | Wiley |
| 5,997,541 A | 12/1999 | Schenk |
| 6,007,566 A | 12/1999 | Wenstrom, Jr. |
| 6,024,758 A | 2/2000 | Thal |
| 6,030,406 A | 2/2000 | Davis et al. |
| 6,045,574 A | 4/2000 | Thal |
| 6,083,522 A | 7/2000 | Chu et al. |
| 6,156,039 A | 12/2000 | Thal |
| 6,258,093 B1 | 7/2001 | Edwards et al. |
| 6,270,501 B1 | 8/2001 | Freiberg et al. |
| 6,306,159 B1 | 10/2001 | Schwartz et al. |
| 6,312,438 B1 | 11/2001 | Adams |
| 6,364,886 B1 | 4/2002 | Sklar |
| 6,383,188 B2 | 5/2002 | Kuslich et al. |
| 6,416,517 B2 | 7/2002 | Harder et al. |
| 6,431,801 B2 | 8/2002 | Vasudeva et al. |
| 6,436,124 B1 | 8/2002 | Anderson et al. |
| 6,474,425 B1 | 11/2002 | Truax et al. |
| 6,494,272 B1 | 12/2002 | Eppink et al. |
| 6,508,830 B2 | 1/2003 | Steiner |
| 6,730,092 B2 | 5/2004 | Songer |
| 6,746,451 B2 | 6/2004 | Middleton et al. |
| 6,783,533 B2 | 8/2004 | Green et al. |
| 6,824,552 B2 | 11/2004 | Robison et al. |
| 6,874,978 B2 | 4/2005 | Gongola |
| 6,887,259 B2 | 5/2005 | Lizardi |
| 7,018,144 B2 | 3/2006 | Sasagawa et al. |
| 7,029,479 B2 | 4/2006 | Tallarida et al. |
| 7,041,107 B2 | 5/2006 | Pohjonen et al. |
| 7,048,755 B2 | 5/2006 | Bonutti et al. |
| 7,217,279 B2 | 5/2007 | Reese |
| 7,258,692 B2 | 8/2007 | Thelen et al. |
| 7,381,213 B2 | 6/2008 | Lizardi |
| 7,488,322 B2 | 2/2009 | Brunnett et al. |
| 7,488,329 B2 | 2/2009 | Thelen et al. |
| 7,520,898 B2 | 4/2009 | Re et al. |
| 7,578,836 B2 | 8/2009 | Justin et al. |
| 7,651,509 B2 | 1/2010 | Bojarski et al. |
| 7,678,134 B2 | 3/2010 | Schmieding et al. |
| 7,803,173 B2 | 9/2010 | Burkhart et al. |
| 7,892,235 B2 | 2/2011 | Ellis |
| 7,909,547 B2 | 3/2011 | Jordan et al. |
| 7,963,967 B1 | 6/2011 | Woods |
| 7,981,140 B2 | 7/2011 | Burkhart |
| 8,002,733 B2 | 8/2011 | Kraft et al. |
| 8,043,253 B2 | 10/2011 | Kraft et al. |
| 8,070,750 B2 | 12/2011 | Wenstrom, Jr. et al. |
| 8,109,700 B2 | 2/2012 | Jordan et al. |
| 8,231,674 B2 | 7/2012 | Albertorio et al. |
| 8,312,942 B2 | 11/2012 | Ho et al. |
| 8,366,713 B2 | 2/2013 | Long et al. |
| 8,394,129 B2 | 3/2013 | Morgenstern Lopez et al. |
| 8,439,976 B2 | 5/2013 | Albertorio et al. |
| 8,469,998 B2 | 6/2013 | Sojka et al. |
| 8,512,340 B2 | 8/2013 | Easley et al. |
| 8,518,087 B2 | 8/2013 | Lopez et al. |
| 8,556,911 B2 | 10/2013 | Mehta et al. |
| 8,597,333 B2 | 12/2013 | Morgenstern Lopez et al. |
| 8,623,051 B2 | 1/2014 | Bojarski et al. |
| 8,663,324 B2 | 3/2014 | Schmieding et al. |
| 8,801,800 B2 | 8/2014 | Bagga et al. |
| 8,814,905 B2 | 8/2014 | Sengun et al. |
| 8,821,543 B2 | 9/2014 | Hernandez et al. |
| 8,821,544 B2 | 9/2014 | Sengun et al. |
| 8,821,545 B2 | 9/2014 | Sengun |
| 9,072,530 B2 | 7/2015 | Mehta et al. |

(56) References Cited

U.S. PATENT DOCUMENTS

| | | |
|---|---|---|
| 9,451,938 B2 | 9/2016 | Overes et al. |
| 2001/0027320 A1 | 10/2001 | Sasso |
| 2002/0040241 A1 | 4/2002 | Jarvinen |
| 2002/0183758 A1 | 12/2002 | Middleton et al. |
| 2003/0032961 A1 | 2/2003 | Pelo et al. |
| 2003/0191487 A1* | 10/2003 | Robison ............ A61B 17/32002 606/170 |
| 2003/0195565 A1 | 10/2003 | Bonutti |
| 2004/0010287 A1 | 1/2004 | Bonutti |
| 2004/0049194 A1 | 3/2004 | Harvie et al. |
| 2004/0149093 A1 | 8/2004 | Tang |
| 2004/0193168 A1 | 9/2004 | Long et al. |
| 2004/0208717 A1 | 10/2004 | Greenhalgh |
| 2004/0267317 A1 | 12/2004 | Higgins et al. |
| 2005/0038427 A1 | 2/2005 | Perriello et al. |
| 2005/0137600 A1 | 6/2005 | Jacobs et al. |
| 2005/0147478 A1 | 7/2005 | Greenberg |
| 2005/0203527 A1 | 9/2005 | Carrison et al. |
| 2005/0261604 A1 | 11/2005 | Stephens et al. |
| 2005/0283156 A1 | 12/2005 | Schmieding et al. |
| 2005/0288710 A1 | 12/2005 | Fallin et al. |
| 2006/0015110 A1 | 1/2006 | Pepper |
| 2006/0079904 A1 | 4/2006 | Thal |
| 2006/0100631 A1 | 5/2006 | Sullivan et al. |
| 2006/0247641 A1 | 11/2006 | Re et al. |
| 2007/0185532 A1 | 8/2007 | Stone et al. |
| 2007/0225721 A1 | 9/2007 | Thelen et al. |
| 2007/0255317 A1 | 11/2007 | Fanton et al. |
| 2007/0260259 A1 | 11/2007 | Fanton et al. |
| 2007/0276392 A1 | 11/2007 | Beyar et al. |
| 2007/0288023 A1 | 12/2007 | Pellegrino et al. |
| 2008/0004659 A1 | 1/2008 | Burkhart et al. |
| 2008/0009904 A1 | 1/2008 | Bourque et al. |
| 2008/0058816 A1 | 3/2008 | Philippon et al. |
| 2008/0065114 A1 | 3/2008 | Stone et al. |
| 2008/0082127 A1 | 4/2008 | Stone et al. |
| 2008/0082128 A1 | 4/2008 | Stone |
| 2008/0109037 A1 | 5/2008 | Steiner et al. |
| 2008/0114364 A1 | 5/2008 | Goldin et al. |
| 2008/0140078 A1 | 6/2008 | Nelson et al. |
| 2008/0140092 A1 | 6/2008 | Stone et al. |
| 2008/0140093 A1 | 6/2008 | Stone et al. |
| 2008/0147063 A1 | 6/2008 | Cauldwell et al. |
| 2008/0147064 A1 | 6/2008 | Cauldwell et al. |
| 2008/0147071 A1 | 6/2008 | Serra et al. |
| 2008/0243163 A1 | 10/2008 | Masseglia et al. |
| 2008/0255613 A1 | 10/2008 | Kaiser et al. |
| 2008/0262544 A1 | 10/2008 | Burkhart |
| 2008/0275431 A1 | 11/2008 | Stone et al. |
| 2008/0275469 A1 | 11/2008 | Fanton et al. |
| 2008/0319478 A1 | 12/2008 | Foerster et al. |
| 2009/0112208 A1* | 4/2009 | Borgia .................. A61B 17/16 606/59 |
| 2009/0112270 A1 | 4/2009 | Lunn et al. |
| 2009/0138042 A1 | 5/2009 | Thal |
| 2009/0157124 A1 | 6/2009 | Ferragamo et al. |
| 2009/0221922 A1* | 9/2009 | Lee ..................... A61B 5/0084 600/478 |
| 2009/0234386 A1 | 9/2009 | Dean et al. |
| 2009/0234451 A1 | 9/2009 | Manderson |
| 2009/0240104 A1 | 9/2009 | Ogdahl et al. |
| 2009/0265002 A1 | 10/2009 | Re et al. |
| 2009/0312792 A1 | 12/2009 | Fallin et al. |
| 2009/0312793 A1 | 12/2009 | Huxel et al. |
| 2010/0049202 A1 | 2/2010 | Re |
| 2010/0145341 A1 | 6/2010 | Ranck et al. |
| 2010/0160962 A1 | 6/2010 | Dreyfuss et al. |
| 2010/0185238 A1 | 7/2010 | Cauldwell et al. |
| 2010/0262146 A1 | 10/2010 | Tulkis |
| 2010/0292731 A1 | 11/2010 | Gittings et al. |
| 2010/0292732 A1 | 11/2010 | Hirotsuka et al. |
| 2011/0015674 A1 | 1/2011 | Howard et al. |
| 2011/0015675 A1 | 1/2011 | Howard et al. |
| 2011/0022083 A1 | 1/2011 | DiMatteo et al. |
| 2011/0022084 A1 | 1/2011 | Sengun et al. |
| 2011/0046625 A1 | 2/2011 | Boileau et al. |
| 2011/0152927 A1 | 6/2011 | Deng et al. |
| 2011/0208194 A1 | 8/2011 | Steiner et al. |
| 2011/0213416 A1 | 9/2011 | Kaiser |
| 2011/0213417 A1 | 9/2011 | Foerster et al. |
| 2011/0264140 A1 | 10/2011 | Lizardi et al. |
| 2011/0270278 A1 | 11/2011 | Overes et al. |
| 2012/0053591 A1* | 3/2012 | Haines ................. A61B 17/157 606/88 |
| 2012/0053629 A1 | 3/2012 | Reiser et al. |
| 2012/0071976 A1 | 3/2012 | May et al. |
| 2012/0095556 A1 | 4/2012 | Re et al. |
| 2012/0109156 A1 | 5/2012 | Overes et al. |
| 2012/0109194 A1 | 5/2012 | Miller et al. |
| 2012/0123474 A1 | 5/2012 | Zajac et al. |
| 2012/0130424 A1 | 5/2012 | Sengun et al. |
| 2012/0150203 A1 | 6/2012 | Brady et al. |
| 2012/0179254 A1 | 7/2012 | Saliman |
| 2012/0197271 A1 | 8/2012 | Astorino et al. |
| 2012/0209325 A1 | 8/2012 | Gagliano et al. |
| 2012/0290006 A1 | 11/2012 | Collins et al. |
| 2013/0023929 A1 | 1/2013 | Sullivan et al. |
| 2013/0085568 A1 | 4/2013 | Smith et al. |
| 2013/0096611 A1 | 4/2013 | Sullivan |
| 2013/0096612 A1 | 4/2013 | Zajac et al. |
| 2013/0131722 A1 | 5/2013 | Marchand et al. |
| 2013/0144334 A1* | 6/2013 | Bouduban .......... A61B 17/0401 606/232 |
| 2013/0158596 A1 | 6/2013 | Miller et al. |
| 2013/0158601 A1 | 6/2013 | Stone et al. |
| 2013/0165972 A1 | 6/2013 | Sullivan |
| 2013/0178898 A1 | 7/2013 | Arnett et al. |
| 2013/0190818 A1 | 7/2013 | Norton |
| 2013/0190819 A1 | 7/2013 | Norton |
| 2013/0245700 A1 | 9/2013 | Choinski |
| 2013/0296931 A1 | 11/2013 | Sengun |
| 2013/0325063 A1 | 12/2013 | Norton et al. |
| 2013/0345749 A1 | 12/2013 | Sullivan et al. |
| 2014/0039503 A1 | 2/2014 | Pilgeram |
| 2014/0163679 A1 | 6/2014 | Re et al. |
| 2014/0188163 A1 | 7/2014 | Sengun |

FOREIGN PATENT DOCUMENTS

| | | |
|---|---|---|
| EP | 253526 A1 | 1/1988 |
| EP | 0440371 A1 | 8/1991 |
| EP | 1174584 A2 | 1/2002 |
| EP | 1369089 A2 | 12/2003 |
| EP | 1398455 A2 | 3/2004 |
| EP | 2548519 A2 | 1/2013 |
| EP | 2596755 A2 | 5/2013 |
| EP | 2662030 A1 | 11/2013 |
| EP | 2662032 A1 | 11/2013 |
| FR | 2676638 A1 | 11/1992 |
| WO | 9628100 A1 | 9/1996 |
| WO | 9704908 A1 | 2/1997 |
| WO | 9722301 A1 | 6/1997 |
| WO | 0044291 A1 | 8/2000 |
| WO | 0128457 A1 | 4/2001 |
| WO | 0160268 A1 | 8/2001 |
| WO | 03/092514 A1 | 11/2003 |
| WO | 2004092531 A2 | 10/2004 |
| WO | 2007/010389 A1 | 1/2007 |
| WO | 2009105880 A1 | 9/2009 |

OTHER PUBLICATIONS

European Search Report, EP 10173568, dated Nov. 30, 2010.
Extended European Search Report for Application No. EP 12164104 dated Jul. 11 2012.
Extended European Search Report for Application No. EP14157129 dated Oct. 9, 2014.
Extended European Search Report for Application No. EP14159656 dated Jun. 6, 2014.
International Search Report and Written Opinion for Application No. PCT/US2014/021231 dated Jun. 25, 2014.
International Search Report and Written Opinion for Application No. PCT/US2014/069087 dated Jun. 17, 2015.

(56) References Cited

OTHER PUBLICATIONS

International Search Report PCT/US2010/042264, dated Sep. 30, 2010.
Partial European Search Report for Application No. 13162591 dated Aug. 14, 2015.
Partial International Search Report for Application No. PCT/US2014/069087 dated Mar. 12, 2015.
Perthes, German Surgery Periodical, vol. 85, Commermorative Publication, pp. 2-18, 1906.
Perthes, Über Operationen bel habitueller Schulterluxaton, Deutsch Zeitschrift für Chirurgie, vol. 85, 1906, pp. 199-227 (English translation provided.).

* cited by examiner

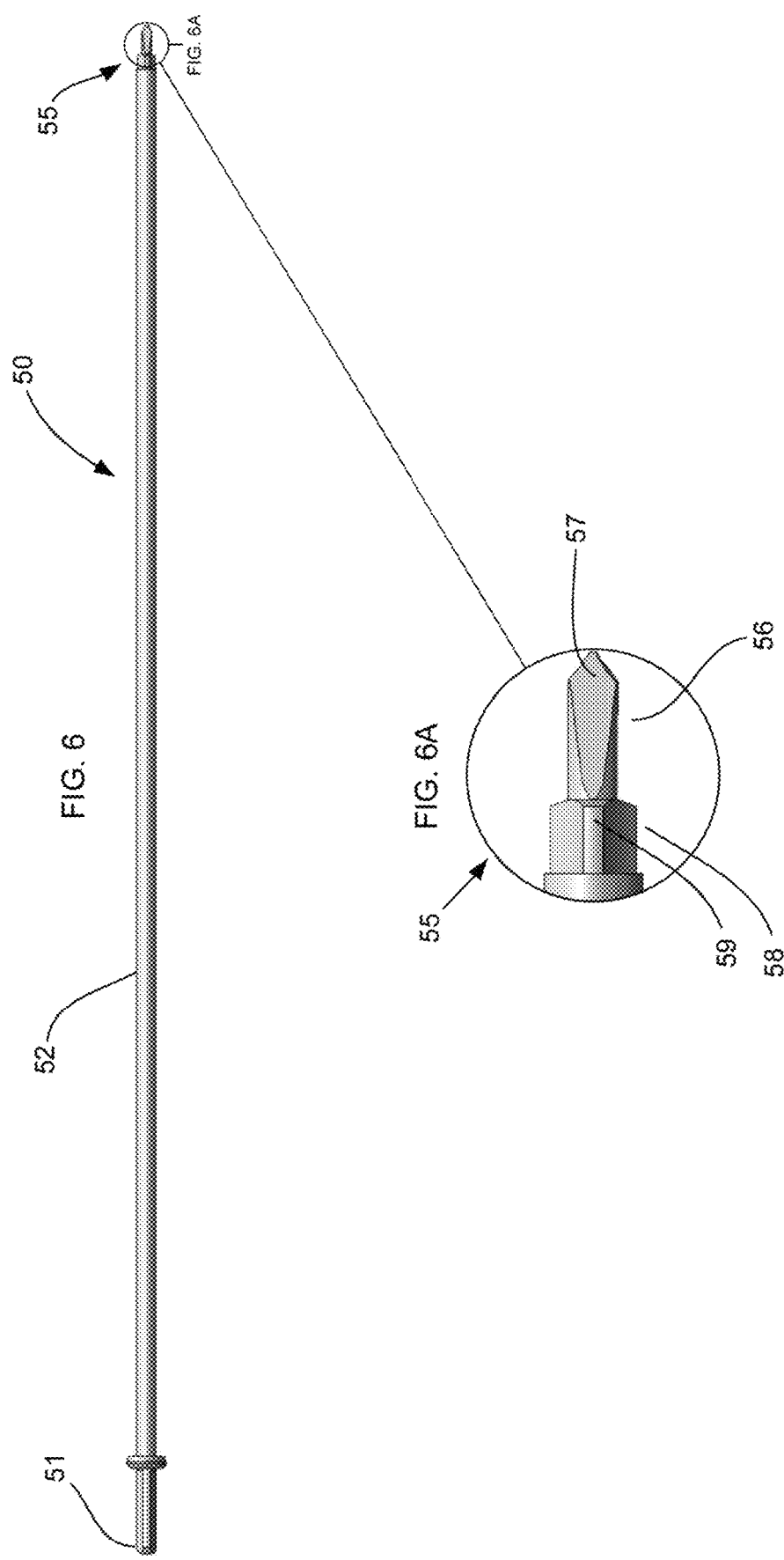

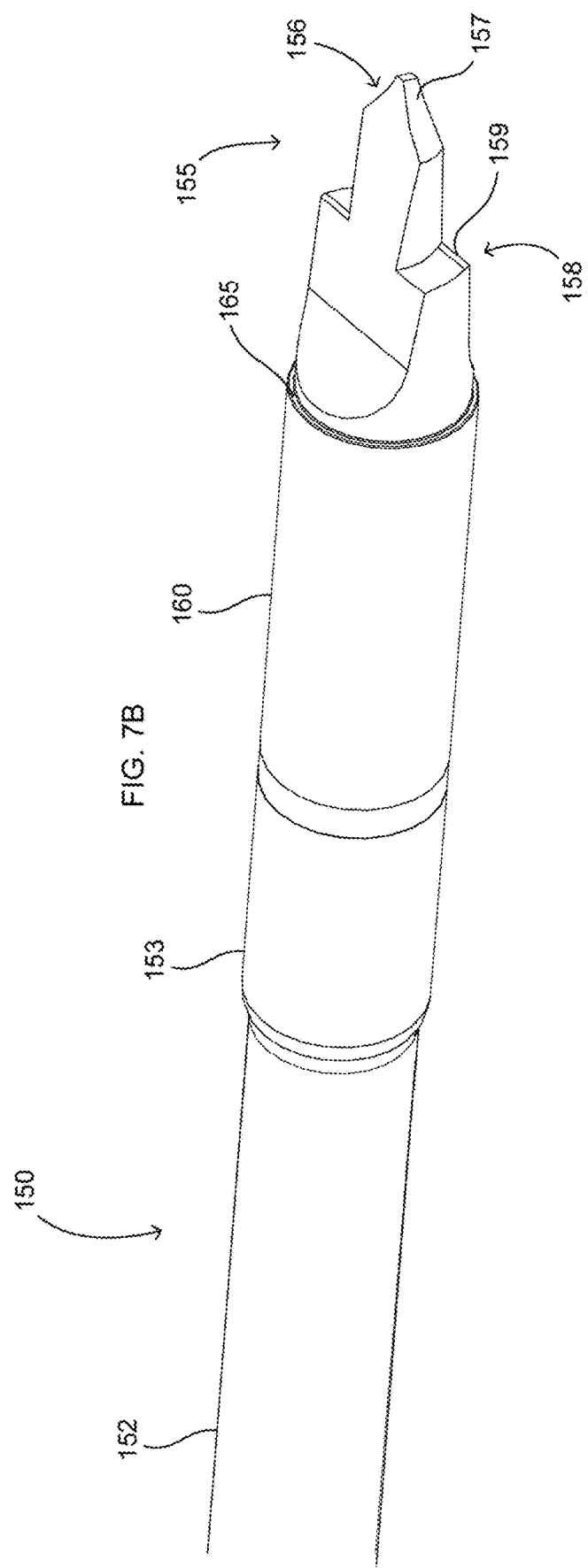

KNOTLESS FILAMENT ANCHOR FOR SOFT TISSUE REPAIR

CROSS-REFERENCE TO RELATED APPLICATIONS

The present application is a divisional of U.S. patent application Ser. No. 14/308,208, filed Jun. 18, 2014, which is a continuation of U.S. patent application Ser. No. 13/441,290, filed Apr. 6, 2012, the disclosures of which are incorporated herein by reference.

BACKGROUND OF THE INVENTION

Various shoulder injuries may result from dislocations and other injuries resulting from traumatic events such as falling or blunt force, or from repetitive motions such as throwing or lifting. A common shoulder injury includes the separation of the glenoid labrum from the glenoid. For example, a Bankart lesion results from a labrum tear that occurs in the anterioinferior region of the glenoid socket when the shoulder dislocates. A superior labrum anterior posterior (SLAP) lesion typically occurs from throwing injuries, where the tear occurs at the superior region of the glenoid socket where the biceps tendon attaches to the shoulder. These injuries result in pain and instability of the shoulder joints.

Arthroscopic stabilization for surgical treatment of shoulder instability has grown in popularity over the past decade. In particular, tissue anchors have been employed to repair torn labrum tissue. For example, a tissue anchor may be inserted into the glenoid, and a suture material that is attached to the anchor is used to reattach the torn labrum tissue to the glenoid.

Tissue anchors have similarly been used in other tissue repair procedures directed towards the rotator cuff, labrum tissue of the hip, and the like. Similar to the labrum repair above, such surgeries typically include placing a tissue anchor into bone at or adjacent to the site of tissue attachment (commonly at or adjacent to the native attachment site) and utilizing a suture to draw the tissue to be reattached towards the tissue anchor and thus, towards the bone. The suture is secured in a known fashion, such as by tying a knot, and the repair is complete.

Knotless tissue anchors have grown in popularity in recent years for use in these types of surgical procedures. Knotless tissue anchors, as commonly defined, do not require the tying of knots by an operator (e.g., surgeon) to secure the tissue to the bone. Instead, the anchor has another type of locking feature which secures the suture, and thus the tissue, without the tying of knots. Such anchors have grown in popularity due to their ease of use and simplification of the surgical procedure by, for example, eliminating the need for knot pusher instruments and the like.

However, currently used "knotless" tissue anchors typically still include a knot somewhere along the suture such that, even though the operator may not be required to tie a knot during the surgical procedure, the suture still includes a knot, typically pre-tied by the anchor manufacturer, along its length. This knot, over time and with repeated use, will tighten, thereby loosening the repair. In the example of a labrum repair, such tightening of the knot may loosen the repair such that the labrum is no longer positioned snugly against the bone surface. Such loosening may occur even if the suture remains intact.

Therefore, there is room for improvement over existing "knotless" anchors, particularly with regard to, for example, further simplification of insertion of such anchors, as well as better assurance of replication of the procedure. Additionally, there is a need in the art for a truly knotless tissue anchor which does not include any knots, whether pre-tied or tied by the operator, in the suture.

BRIEF SUMMARY OF THE INVENTION

In one embodiment, the present invention includes a method for securing tissue to bone, including drilling a bone hole into the bone; passing a filament through the tissue, the filament including a first end, a second end and a length therebetween, the second end having a loop; passing the first end of the filament through the loop of the filament; pulling on the first end of the filament such that the loop travels along the length of the filament and to the tissue; passing an anchor along the length of the filament, from the first end towards the loop and tissue; engaging the loop with a distal end of the anchor; positioning the distal end of the anchor, with the loop of the filament, into the bone hole; and securing the anchor in the bone.

Further, the step of drilling the bone hole further may include drilling a first portion of the bone hole to a first diameter and a second portion of the bone hole to a second diameter, wherein the first diameter is smaller than the second diameter. The drill may further include a bushing, such that the step of drilling also includes the step of marking the surface of the bone surrounding the bone hole with a distal face of the bushing. The distal face of the bushing may include a marking material. Also, the step of securing the anchor in the bone may further include directing the anchor into the second portion of the bone hole and forcing the anchor through the second portion and into the first portion of the bone hole. The anchor may continue to be forced into the bone hole such that the anchor may be forced through the first portion of the bone hole and further into the bone past the first portion of the bone hole. Moreover, the anchor may be engaged with an inserter with which an operator performs the steps of passing the anchor towards the loop and tissue, positioning the distal end of the anchor into the bone hole, and securing the anchor in the bone. The method may further include positioning a cannulated guide adjacent to the tissue and bone, such that the steps of the above method, including for example the drilling, passing and positioning steps, may be performed at least partially through the cannulated guide.

In another embodiment, the present invention may include a system for securing tissue to bone, including a drill; a filament having a first end and a second end, the second end including a loop; and an anchor having a distal end and a proximal end, wherein the distal end is capable of engaging the loop of the filament.

The drill may include a boring structure, on a distal end of the drill, having a first diameter at a distal end and a second diameter proximal of the first diameter, wherein the second diameter is larger than the first diameter. The anchor has a diameter, wherein the diameter of the anchor may be larger than the first diameter of the drill and substantially the same size as the second diameter. Alternatively, the diameter of the anchor may be smaller than the second diameter. The system may further include an inserter adapted to engage the anchor at the proximal end. Further, the anchor may be cannulated and the inserter may be at least partially cannulated, such that the cannulated anchor and inserter are adapted to position a portion of the first end of the filament therein.

In yet another embodiment, the present invention may include a drill having a boring structure having a first diameter at a distal end and a second diameter proximal of the first diameter, wherein the second diameter is larger than the first diameter. The drill may further include at least one flute at the distal end, having the first diameter, and another at least one flute having the second diameter, positioned proximal to the at least one flute at the distal end. The drill may also include a shaft, proximal to the boring structure, wherein the shaft may include a flexible portion.

In a further embodiment, the present invention may include a drill having a distal boring structure and a shaft proximal to the distal boring structure, and a bushing positioned on the shaft proximal to the distal boring structure. The bushing may further include a distal face, wherein at least a portion of the distal face is exposed around at least a portion of the distal boring structure. The distal face may include a marking material positioned thereon adapted to mark a surface of the bone. The surface of the bone may include the bone surface surrounding a prepared bone hole prepared by the distal boring structure. Further, the bushing may be adapted to prevent the drill from creating a bone hole having a depth greater than a length measured from the distal-most portion of the distal boring structure to the distal face of the bushing.

In another embodiment, the present invention may include a filament having a length between a first end and a second end, the second end including a loop, and at least a portion of the filament having a construction including a substantially solid thickness. For example, at least a portion of the loop may include a substantially solid thickness (e.g., monofilament structure). Alternatively, at least a portion of the length between the first and second ends may include a substantially solid thickness.

In yet a further embodiment, the present invention may include a filament having a length between a first end and a second end, the second end including a loop, the filament also including at least one marking along its length. The marking may be located on at least a portion of the loop. Alternatively, the marking may be located on at least a portion of the length between the first and second ends. Additionally, multiple markings may be positioned at various locations on the filament. The markings may include, for example, a spot, a radial ring, a portion having a differing color from the rest of the filament, or the like.

In another embodiment, the present invention may include a method of repairing tissue, including passing a first filament through the tissue at a first location, the filament including a length between a first end and a second end, the second end including a loop; passing the first end of the filament through the loop and tensioning the first end; preparing a first bone hole at a location in bone adjacent to the tissue, tensioning the first end of the filament in the direction of the bone hole; and securing the first end of the filament at the bone hole using a first suture anchor. The method is performed without the tying of any knots.

The method may further include passing a second filament through the tissue at a second location, the filament including a length between a first end and a second end, the second end including a loop; passing the first end of the second filament through the loop and tensioning the first end; preparing a second bone hole at a second location in bone adjacent to the tissue, tensioning the first end of the second filament in the direction of the second bone hole; and securing the first end of the filament at the second bone hole using a second suture anchor. Alternatively, the second filament may be secured at the first bone hole using the first anchor, such that a second bone hole and second suture anchor is not necessary. The tissue may be a rotator cuff, such that the first bone hole and optional second bone hole are positioned lateral to the rotator cuff tissue.

In yet another embodiment, the present invention may include a method of repairing tissue including passing a first tail of a first filament through the tissue at a first location, the filament including at least two tails, each tail having a length between a first end and a second end, the second end of each tail ending at a common loop; passing the first end of the first tail through the loop and tensioning the first end; preparing a first bone hole at a location in bone adjacent to the tissue, tensioning the first end of the first tail in the direction of the bone hole; and securing the first tail of the filament at the bone hole using a first suture anchor; passing a first tail of a second filament through the tissue at a second location, the second filament including at least two tails, each tail having a length between a first end and a second end, the second end of each tail ending at a common loop of the second filament; passing the first end of the first tail of the second filament through the loop of the second filament and tensioning the first end; preparing a second bone hole at a location in bone adjacent to the tissue; tensioning the first end of the first tail of the second filament in the direction of the second bone hole; and securing the first tail of the filament at the second bone hole using a second suture anchor; tensioning the second tails of both the first and second filaments; preparing a third bone hole at a location in bone adjacent to the tissue; tensioning the first ends of the second tails of the first and second filaments in the direction of the third bone hole; and securing the second tails of the first and second filaments at the third bone hole using a third suture anchor. This method is performed without the tying of any knots. The first tail and the loop of each filament may substantially surround a portion of tissue. The tissue may be a rotator cuff, and more specifically a torn rotator cuff to be reattached to the bone. The first, second and third bone holes may be positioned laterally relative to the rotator cuff tissue. The method may also include, during the step of tensioning the first ends of the first tails of the first and second filaments, tensioning the tissue in the direction of the tensioning.

BRIEF DESCRIPTION OF THE DRAWINGS

FIG. 6 illustrates one embodiment of the drill of the present invention.

FIG. 6A illustrates a detailed view of the distal end the drill of FIG. 6.

FIGS. 7A and 7B illustrate another embodiment of the drill of the present invention, with FIG. 7B also illustrating the drill with a bushing.

DETAILED DESCRIPTION

The present invention is directed towards a tissue anchor and namely, a tissue anchor for securing tissue to bone. The various embodiments herein are directed towards the use of the tissue anchor for repairing a shoulder labrum, through reattachment of the labrum to the bone at or adjacent to its native attachment site. However, the tissue anchors, methods, systems, and kits of the present invention may be used in the repair of tissues other than the labrum, including, for example, rotator cuff tissue. Other cartilage, ligament, tendons and other such soft tissues may also be repaired by the present invention. The present invention may be used in both arthroscopic and open surgical procedures, though its benefits are perhaps most apparent in arthroscopic applications. Further, the present invention is intended to be completely knotless, such that no knots, whether pre-tied by the manufacturer or tied by the operator (e.g., surgeon) during a surgical procedure, are required along the suture (or other filament used) at any point during the surgical procedure. However, of course, individual operator preference may be such that an operator may incorporate a knot in the suture, despite the present invention being capable of performing the surgical procedure without the incorporation of knots.

Throughout this application, "proximal" or "proximally" is intended to mean closer to the operator or towards the operator, while "distal" or "distally" is intended to mean further from the operator or away from the operator.

Figure 1:
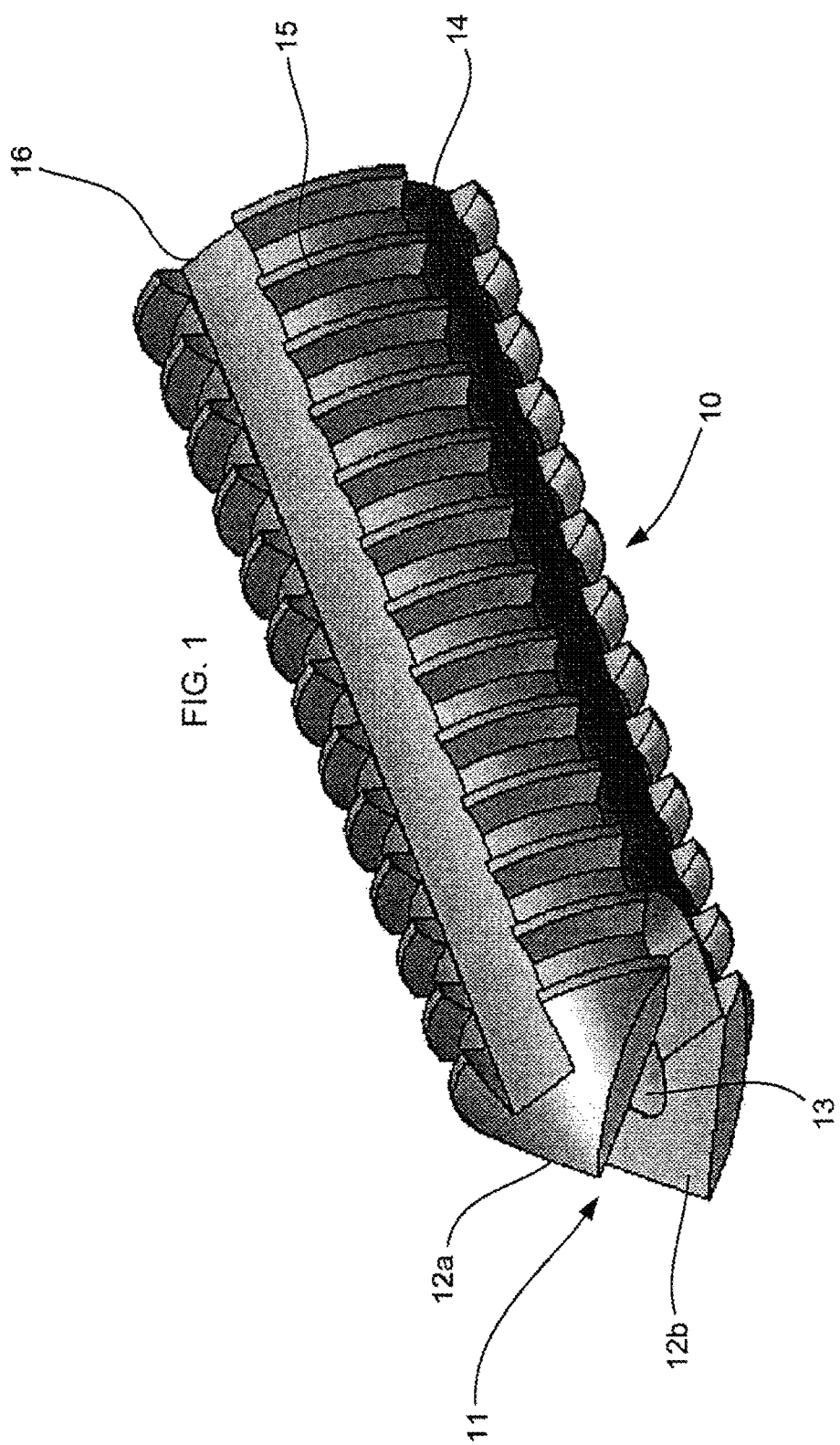
FIG. 1 illustrates one embodiment of the tissue anchor of the present invention.
Figure 2:
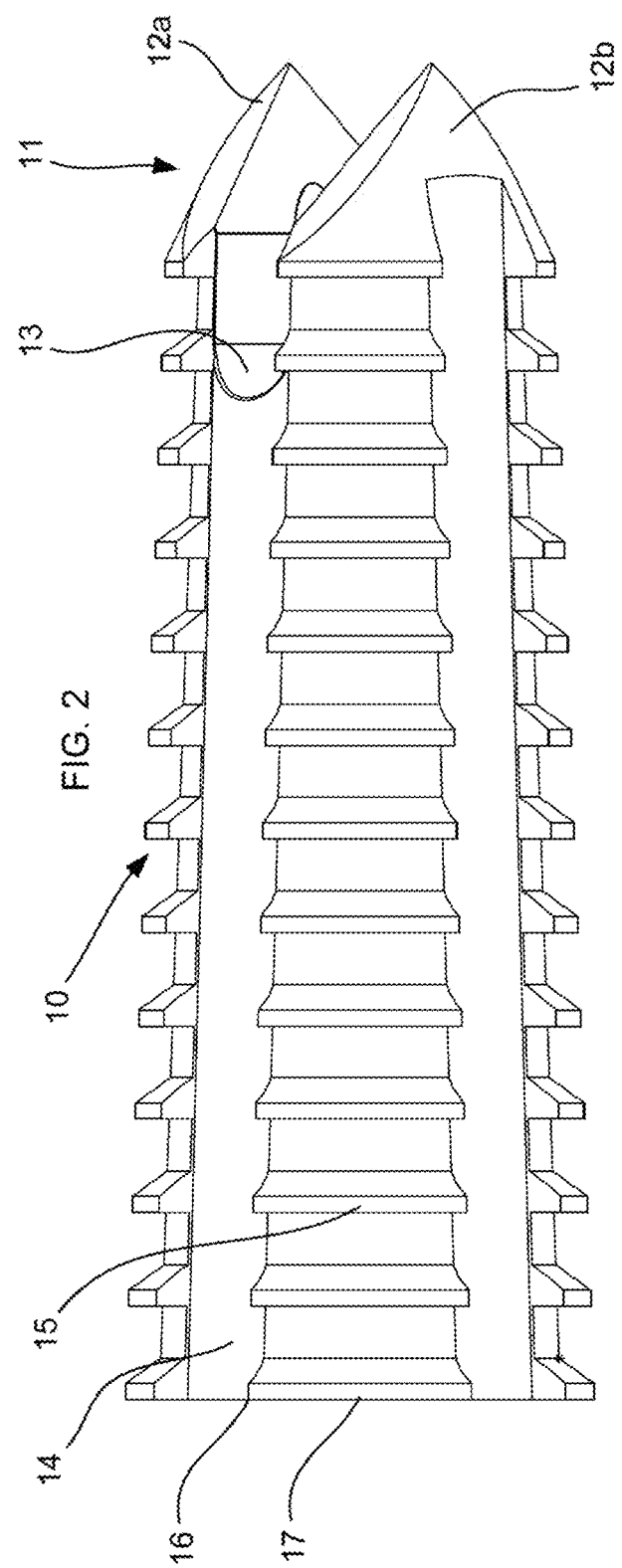
FIG. 2 illustrates a second view of the tissue anchor of FIG. 1.

In one embodiment, the present invention may include an anchor 10 having a distal end 11 and a proximal end 16, as illustrated in FIGS. 1 and 2. The distal end includes tips 12a, 12b and a saddle 13. The anchor 10 also has a length between the distal end and the proximal end and an outer surface along the length. Along at least a portion of the outer surface is at least one groove 14 and at least one ridge 15. The anchor may also have a cannula 17 along at least a portion of its length or, preferably, its entire length. The proximal end 16 may include a structure suitable for engagement by an inserter instrument, such as an indentation from the proximal end 16 through at least a portion of the length of the anchor. Such indentation may include a shape, such as a hexagonal shape, which may match a similar shape on the inserter instrument. Alternatively, in the example of a fully cannulated anchor 10, the structure for engagement by the inserter instrument may be positioned on the proximal end 16 of the anchor 10 between the outer surface and the cannula 17.

Figure 3:
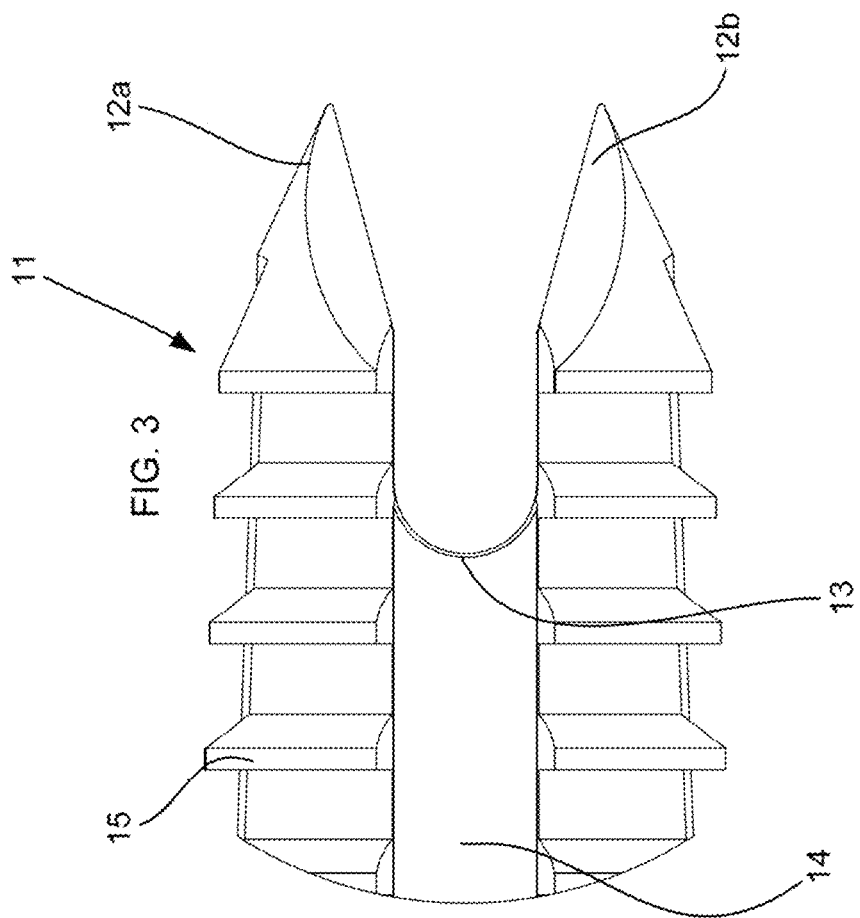
FIG. 3 illustrates a detailed view of a distal end of the tissue anchor of FIGS. 1 and 2.

FIG. 3 illustrates the distal end 11 of the embodiment of FIGS. 1 and 2. The distal end 11 is shaped to accommodate a filament thereon, for example, on saddle 13. Further, the tips 12a, 12b are shaped to at least engage bone, though at least one tip may also be shaped to engage the filament. In this embodiment, the tips 12a, 12b both have a generally triangular shape which may provide a self-tapping or self-boring aspect to the anchor 10 upon insertion of the anchor into the bone. Further, such a shape may also allow at least one tip to engage the filament, such as by piercing or otherwise catching the filament.

The anchor 10 may have a sufficient size for use in an intended surgical procedure such that it provides sufficient pullout strength to the repair while being able to pass through instrumentation, such as a cannulated guide (discussed below). Moreover, the anchor 10 may be of a sufficiently small size to allow for a surgical site of reduced size, including a smaller diameter bone hole than is commonly used in such surgeries. In one example, the anchor 10 may be about 10 mm in length, with a diameter, from ridge 15 to ridge 15, of from about 2 mm to about 4 mm, and specifically between about 2.75 mm to about 3.75 mm, and more specifically about 3.50 mm. The length and diameter dimensions depend on, for example, the intended use and anatomical location of the anchor, and thus other dimensions are also envisioned. For example, if the anchor 10 is used for tissue repair in smaller joints, such as in the ankle, foot or hand, then the dimensions would be significantly smaller than those described above. The saddle 13, between tips 12a, 12b may be dimensioned to accommodate a filament therein, and as such the width of the saddle may be dependent on the size of filament to be positioned on the saddle. For example, the saddle may have a width of less than 1 mm, and more specifically about 0.80 mm, to accommodate a filament having a similarly sized diameter.

The anchor 10 may be constructed from any material suitable for implantation into the body, including, for example, metal, such as titanium, or polymer, such a PEEK.

Figure 4:
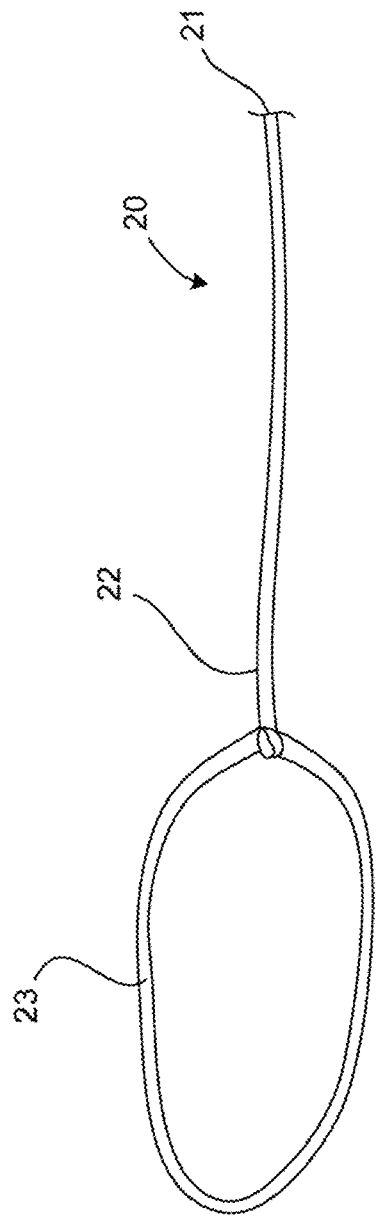
FIG. 4 illustrates one embodiment of the filament of the present invention.

This embodiment may also include filament 20, as illustrated in FIG. 4, which includes a first end 21 and a second end 22, where the second end may further include a loop 23. The portion of the first and second ends, extending from loop 23, forms a length of filament, or a tail. The filament may be of any material, such as a suture or the like, suitable for use in surgical and namely orthopedic applications. The first end 21 may include a portion treated such that it is less flexible that the rest of the filament 20. For example, a portion of the first end 21, extending from the end of the filament and along a certain length of filament from the end, may have a greater stiffness than the remainder of the length of the filament 20. Such a stiff end may be useful, as discussed below, in assisting the operator in threading the first end 21 through the cannulated anchor 10, a cannulated instrument, or the like. The filament may be sized such that a portion of the filament, such as loop 23, may be accommodated within the saddle 13 of anchor 10.

The loop 23 may be woven during manufacture of the filament 20, such that a knot is not required to form the loop 23. Weaving the loop, for example, may eliminate an area of weakness (such as when a knot is used to form a loop) and thus may limit lengthening of the suture during subsequent use by the patient of the repaired tissue. Thus, loop 23 may contribute to increased success of the surgical procedure through the use of the present invention. The size of the loop may vary, depending upon its intended application and/or anatomical location. For example, in some embodiments, the loop may have a diameter of at least about 2 mm. This diameter may be in the range of from about 2 mm to about 25 mm, though larger and smaller sized loops may also be used for particular applications. In some examples, the loop 23 may be about 2 mm, about 10 mm, or about 25 mm, or other sizes in between.

Figure 5:
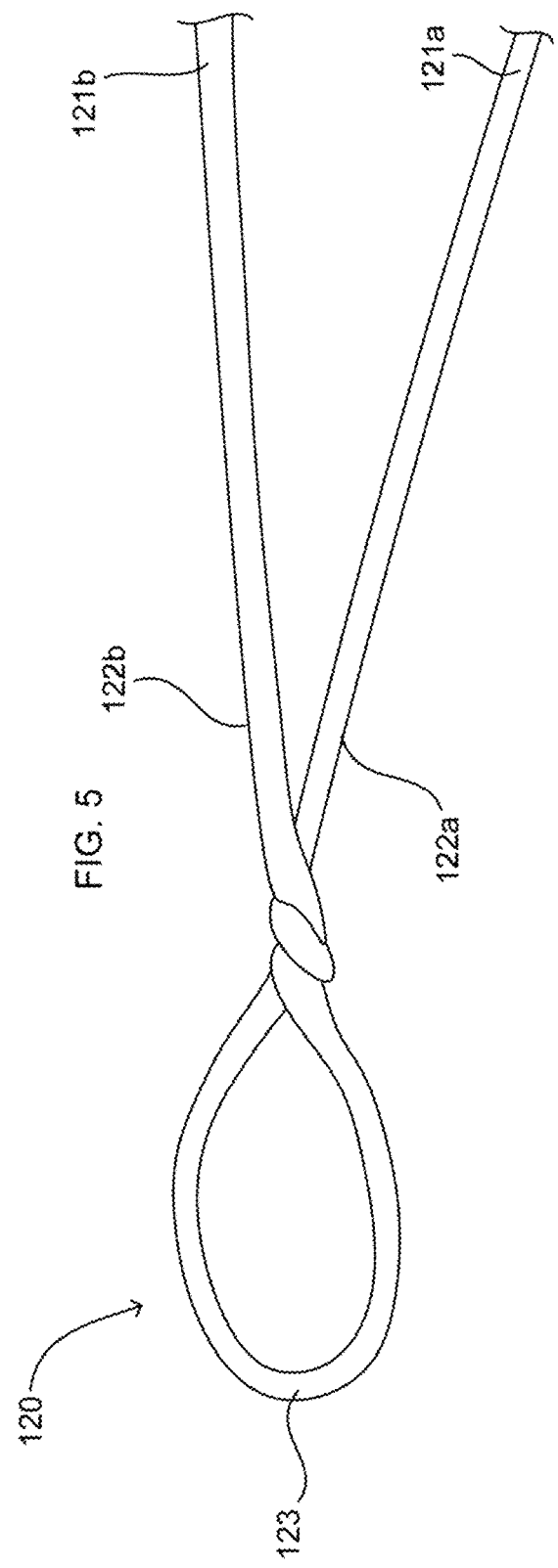
FIG. 5 illustrates another embodiment of the filament of the present invention.

In an alternative embodiment, as illustrated in FIG. 5, the filament 120 may include, extending from the loop 123, two discrete lengths of filament, or tails, extending from second ends 122a, 122b adjacent to the loop and each terminating to a first end 121a, 121b, respectively. Of course, filaments including multiple discrete lengths, and multiple loops, are also envisioned. These discrete lengths may be useful in some method embodiments where, for example, multiple anchors and/or multiple tissues are involved. Examples of such methods are discussed below.

In yet another embodiment, at least a portion of the filament 20, 120 may include an at least one indicating marker (not shown) along its length. Such markings may be similar to those disclosed in co-pending U.S. application Ser. No. 13/303,849, filed Nov. 23, 2011, the entirety of which is incorporated by reference herein as if fully set forth herein. For example, such indicating marker may be, for example, a spot, a radial ring, a portion having a differing color from the rest of the filament, or the like. In another example, the indicating marker may be a portion of the filament 20, 120 being of a different color than the rest of the filament. Such contrasting colors of these portions may provide a clear indication to the operator when performing a surgical procedure, and may be of particular use in arthroscopic procedures. In another example, using filament 120, the first tail (121a, 122a) may be one color and the second tail (121b, 122b) may be a different color from the first tail such that the operator may easily distinguish between the two. In yet another example, the loop 23, 123 of filament 20, 120 may have a marking which may be used by the operator to ensure a sufficient amount of the loop 23, 123 is around the tissue to provide for adequate fixation of the tissue. In this example, the marking may be hidden from the operator, once the loop is in the luggage-tag configuration, which would notify the operator that a sufficient amount of tissue has been grasped within the loop. However, if the marking can still be seen by the operator (when the loop is in the luggage tag configuration), that may indicate to the operator that too little tissue has been grasped within the loop, and thus that the operator should repeat that step. Of course, other variations of such markings may also be used.

Moreover, in yet another embodiment, the filament 20, 120 of the present invention may also include at least a portion of its length having a monofilament structure. For example, the monofilament structure is essentially a portion of the filament which does not have a hollow core, as is typical of most surgical filaments, such as suture. Instead, the hollow core is filled with additional strands of filament to create a substantially solid filament. In one example, the loop 23, 123 may include such a monofilament structure. Alternatively, a portion of the tail, or tails, may also include a monofilament structure along at least a portion of its length.

FIGS. 6 and 6A illustrate one embodiment of a drill 50 having a proximal end 51 and a distal end 55 and a length of shaft 52 therebetween. The drill may be either reusable or disposable. The drill may be manufactured of stainless steel, nitinol, or other biocompatible material.

The distal end 55 of drill 50 constitutes a boring structure which includes a first portion 56 having a first diameter and a second portion 58 having a second diameter. Both first and second portions include at least one flute 57, 59 (respectively) shaped and dimensioned to create a hole in bone. This configuration of the distal end 55 may create a "stepped" bone hole, in that the bone hole includes, for example, a distal portion having a diameter substantially equal to the first diameter of the first portion 56 and a proximal portion having a diameter substantially equal to the second diameter of the second portion 58. In one example, such a bone hole preparation may result in the proximal portion being positioned within substantially the entire depth of the cortical bone, such that the second portion 58 of the drill 50 decorticates the bone hole site, while the distal portion of the bone hole is positioned substantially within the underlying cancellous bone, such that the first portion 56 of the drill 50 forms a pilot hole through the cancellous bone to a depth substantially equal to the length of the first portion 56. As discussed below, this pilot hole is only drilled to a partial depth relative to the final depth of the implanted anchor in the bone. This example may result in a bone hole including a decorticated area and a pilot hole into the cancellous bone, though in some surgical sites, where the cortical bone may be thinner than normal, the second portion 58 of the drill may form a hole extending through the cortical bone and into a portion of the cancellous bone.

To further this example, the first and second portions 56, 58 of drill 50 are sized to prepare such a bone hole. Thus, in this example, the length of the first portion 56 may be about 6 mm, and the length of the second portion may be about 3 mm. In an alternative example, the length of the first portion may be about 4 mm, and the length of the second portion may be about 4 mm. While the length of the second portion should be sufficient to decorticate the entire depth of the cortical bone at the surgical site, the length of the first portion may have any length desired and may be designed with a specific surgical procedure in mind or, alternatively, may be a fixed length which is suitable for most intended surgical procedures.

The first and second diameters of the first and second portions 56, 58 of drill 50 may also vary dependent upon, for example, the size of the tissue anchor to be positioned and secured within the bone hole. The first portion 56 may include a diameter which is smaller than the diameter of the tissue anchor to be implanted within the bone hole, thus forming a pilot hole relative to the anchor to be implanted. Using the above dimensions for anchor 10 as a reference point for this example, the first diameter of the first portion 56 of the drill 50 would be less than, for example, 3.50 mm, and specifically, less than about 2 mm, and more specifically, about 1.5 mm. The second diameter, of the second portion 58, again using anchor 10 as a reference, would be at least about 3.50 mm, and specifically about 3.70 mm.

The proximal end 51 may include a structure for connection to a power drill, a hand drill, or the like, to rotate the distal end 55.

The shaft 52 of drill 50 may have a diameter, and structure, sufficient to transfer the rotational force from the proximal end 51 to the distal end 55. Thus, for example, the shaft 52, along with the proximal and distal ends, may be manufactured out of metal, such as stainless steel or the like, or other material suitable for a drill used to prepare a bone hole. The diameter of the shaft may be larger than the distal end 55, such as about 4.0 mm, though the shaft should not be too large as to not fit through instrumentation being used, such as a cannula or drill guide.

In another embodiment, the shaft 52 may be flexible such that the drill may pass through a curved cannulated guide or curved drill guide. Such exemplary instrumentation is disclosed in U.S. patent application Ser. No. 12/821,504, filed Jun. 23, 2010, the entirety of which is incorporated by reference herein as if fully set forth herein, as well as in the TwinLoop FLEX Instrumentation System (Stryker Endoscopy, San Jose, Calif.).

Figure 7A:
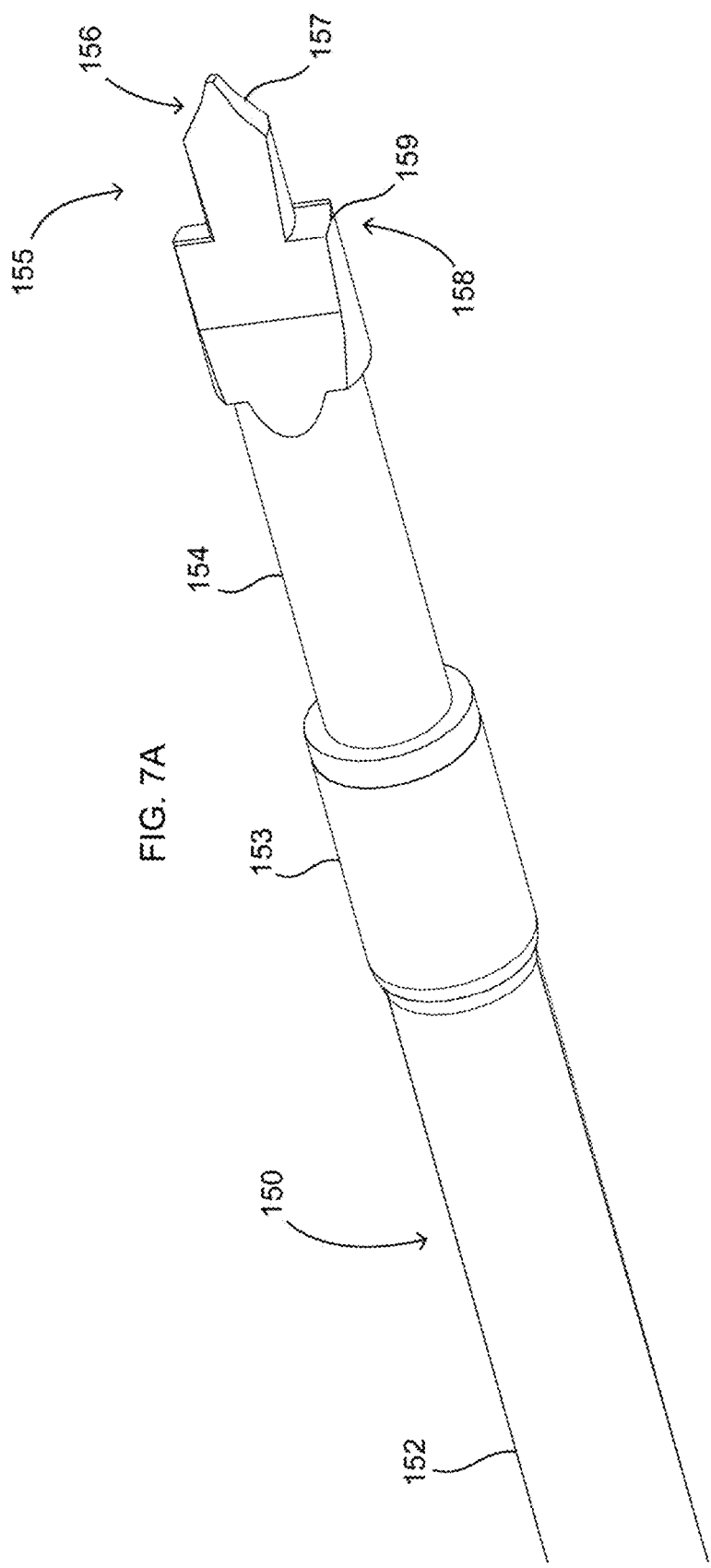

In an alternative embodiment of the drill of the present invention, drill 150 is illustrated in FIGS. 7A-7B. Drill 150 is similar to drill 50 in that a similar bone hole is prepared by either drill. As illustrated in FIGS. 7A, 7B, the distal end 155 constitutes a boring structure, similar to that of FIG. 6A, which includes a first portion 156 having a first diameter and a second portion 158 having a second diameter. Both first and second portions include at least one flute 157, 159 (respectively) shaped and dimensioned to create a hole in bone. This configuration of the distal end 155 also creates the "stepped" bone hole, including, for example, a distal portion having a diameter substantially equal to the first diameter of the first portion 156 and a proximal portion having a diameter substantially equal to the second diameter of the second portion 158.

Drill 150, however, includes a shaft 152 having a stepped portion 153 of a larger diameter than the rest of the length of the shaft. Stepped portion 153 may have a diameter substantially equal to or greater than the second portion 158 which may, for example, ensure that the distal end 155 of the drill 150 remains centered within a cannulated guide, or drill guide, if one is used. Stepped portion may also include a circumferential groove 154 within which a bushing 160 may be positioned.

Bushing 160 may be positioned within groove 154 and may be held in place by the shape of the groove 154, an adhesive, or the like. Bushing may rotate along with the drill or may be capable of rotation independent of the drill such that, for example, bushing 160 may remain in a stationary position even while the drill is rotating during use. Bushing may be manufactured of plastic or other biocompatible material, such as for example, PEEK. Bushing 160 may also assist in maintaining the drill 150 in a centered position within a cannulated guide, or drill guide. Bushing 160 may have a diameter that is substantially equal to the stepped portion 153 to maintain a smooth, generally continuous surface along the shaft. Furthermore, the bushing 160 may serve as a visual indicator for the operator to determine the depth of the drill in the bone. For example, the bushing may have a different color than the drill shaft, such that the contrasting colors serve as the visual indicator to the operator. Of course, even with the contrasting colors, the shaft may still include a laser marking (e.g., proximal to the bushing), which may serve as an additional visual indicator.

Additionally, bushing 160 may include a distal face 165, at least a portion of which is exposed, as illustrated in FIG. 7B. If bushing is to be used with drill 150, as in FIG. 7B, the distal end 155 may be narrowed in at least one dimension, such that as much of the distal face 165 is exposed as possible. Such narrowing of the distal end 155, in one example, may result in the flatter-shaped distal end illustrated in FIGS. 7A and 7B as opposed to the generally circular-shaped distal end 55 of the drill 50 of FIGS. 6 and 6A. This distal face 165 may serve as a drill stop to prevent the distal end 155 from proceeding too deeply into the bone. Distal face 165 may also include a marking material applied to its surface. The marking material may be surgical ink, or the like, which, upon contact with the bone surface (surrounding the prepared bone hole), marks the contacted bone surface with the ink. In use, this marking may assist the operator in locating the bone hole for insertion of the bone anchor 10 (other other anchor). Such marking may be particularly useful in methods of surgery where, for example, the drill is used to create multiple bone holes, or where the bone hole is prepared in an anatomical position difficult to access, such as for example a position under a rotator cuff tissue, or the like.

The bushing 160 may be easily removable from the drill such that the drill may be reused and, each subsequent use, a new bushing may be installed on the groove 154. Alternatively, if the drill is disposable, then the bushing may be positioned on the drill during manufacture (using an adhesive or the like) and, upon using the drill, the operator may dispose of the entire structure. Of course, bushing 165 may also have sufficient marking material on its distal face 165 for multiple surgeries.

In another embodiment, the present invention may include a system including a tissue anchor, a filament and a drill. Such a system may be supplied to the operator in various ways. For example, the drill may be sterilizable and reusable, and thus only the anchor and filament need be supplied for each particular surgical procedure. In this example, the filament and anchor may be sold separately or together as a set. The system may also include a cannulated guide (or drill guide) and an inserter for insertion of the tissue anchor. Thus, in another example, the system may include the anchor, filament, and inserter, and optionally, the drill and/or cannulated guide (or drill guide).

In yet another embodiment, the present invention may also include a kit including at least one anchor and at least one filament. For example, an anchor may be sold with a plurality of filaments such that the operator may determine the appropriate filament for a particular surgical procedure. The plurality of filaments may differ according to, for example, diameter of the filament, length of the tail (or tails) of the filament, size of the loop, number of discrete filament portions or tails extending from the loop, number of loops on the filament, color and/or texture, and the like. In an alternative example, the kit may include a plurality of anchors 10 which may differ according to length, diameter, size of saddle, number and/or shape of the tips, and the like. Alternatively, other anchors (such as those included in the below surgical methods) may be included in such kits with the filament 20, 120 or filaments. Such kits may provide the operator with a selection of options which may be utilized for a particular surgical procedure and/or certain anatomical constraints. Such kits of the present invention may also include any or all of at least one inserter, at least one drill, at least one cannulated guide (or drill guide), or the like. In one example, the kit may also include a plurality of cannulated guides having various angles of curvature for use in various anatomical locations which may be better suited to using curved instrumentation. Of course, such kits may also include a cannulated guide that is linear or straight.

The devices, systems and kits of the present invention may be used in various methods of surgery. As discussed above, the below methods are specific to labrum repair or rotator cuff repair in the shoulder, though such methods are also applicable to, for example, labrum repair in the hip as well as the repair of other soft tissues. The devices, systems and kits, having smaller dimensions than those discussed above, may also be used in small joint surgical methods and procedures, such as ankle, hand and foot soft tissue repairs. Moreover, these methods of surgery are described as to arthroscopic repair, though other forms of surgery, such as open surgery, are also envisioned.

Figure 8C:
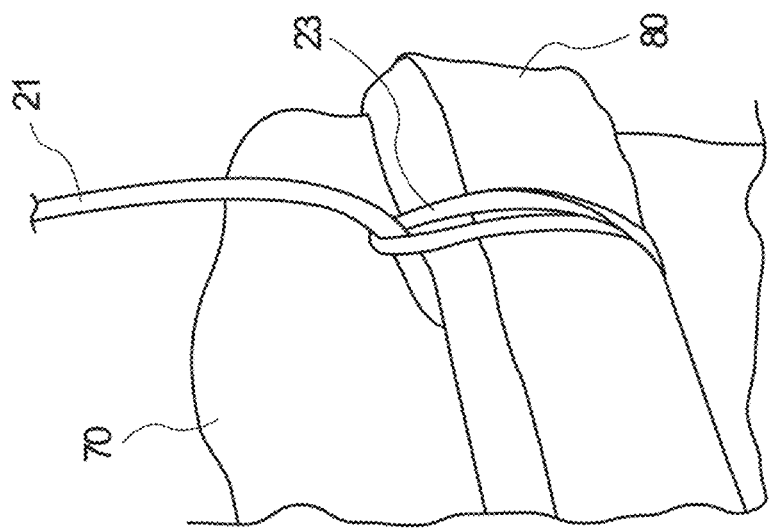
FIGS. 8A-8L illustrate various steps of one embodiment of a method of the present invention as exemplified using a model bone block.
Figure 8B:
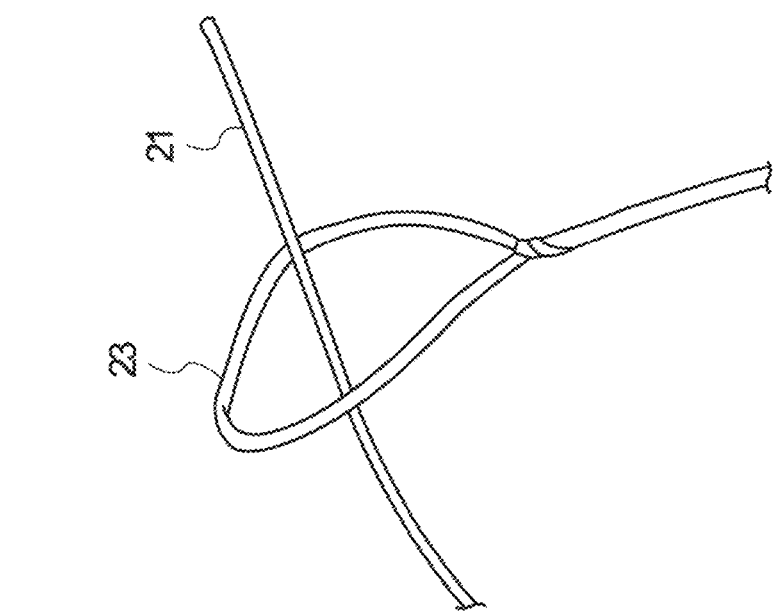
Figure 8A:
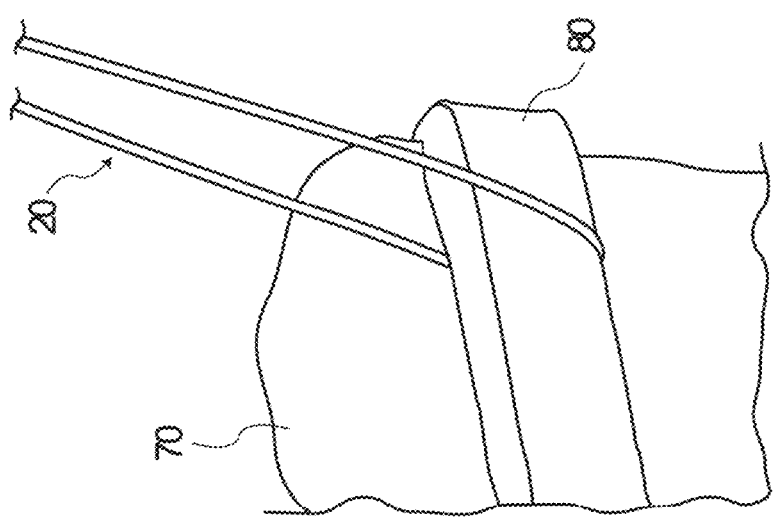
Figure 8E:
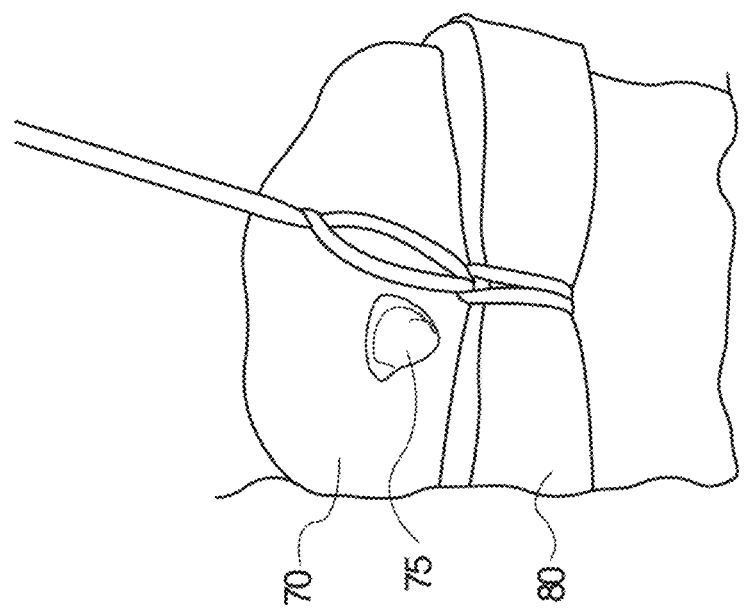

In one embodiment, illustrated in FIGS. 8A-L, a method of the present invention may be used to secure tissue 80 to bone 70, for example, to repair a tear in the labrum to reattach the labrum to the bone at or adjacent to the native attachment site. Upon accessing the surgical site (e.g., the labrum tear from the glenoid), a cannulated guide (such as any of the "guides" 12, 14, 16, 18, 20 disclosed in U.S. patent application Ser. No. 12/821,504, incorporated by reference above, though of course an additional, outer surgical cannula, as is well known for arthroscopic procedures, may also be present outside of such "guides") is optionally positioned through the opening in the surface tissues such that a distal end of the cannulated guide may be positioned adjacent to the surgical site. A drill, such as those illustrated in FIGS. 6-7, is then passed through the cannulated guide (if present) until the distal end 55 of the drill is positioned adjacent to the area of the glenoid (bone 70) where the labrum (tissue 80) will be reattached. The bone hole 75 is then formed using the drill (FIG. 8E). The drill optionally includes a laser mark (not shown), or the like, such that the operator can drill to a proper, predetermined depth. Alternatively, the drill may have a physical stop (not shown), such as at the proximal-most end of the shaft 52, which abuts against the proximal-most end of the cannulated guide and prevents the operator from drilling into the bone any further than the length of the distal end 55. Bushing 160 (FIG. 7B) may also serve as the physical stop. Upon completion of the bone hole 75, the drill is removed from the cannulated guide. A filament 20, such as is illustrated in FIG. 4, is then passed through the cannulated guide (if present) to the detached labrum 80, and the filament is passed around the labrum using known means (FIG. 8A). If using the filament of FIG. 4, either of the first end 21 or the second end 22, having loop 23, may be passed around the labrum 80. In an alternative, the cannulated guide, if used during the preparation of the bone hole, may be removed prior to the step of passing the filament 20 to and around the labrum tissue. In another alternative, rather than the filament 20 passing around the soft tissue 80, the filament may alternatively be passed through the tissue 80. Passing the filament 20 through the tissue 80 may have the benefit of maintaining separation between the filament 20 and the articulating surface of the shoulder joint.

Figure 8D:
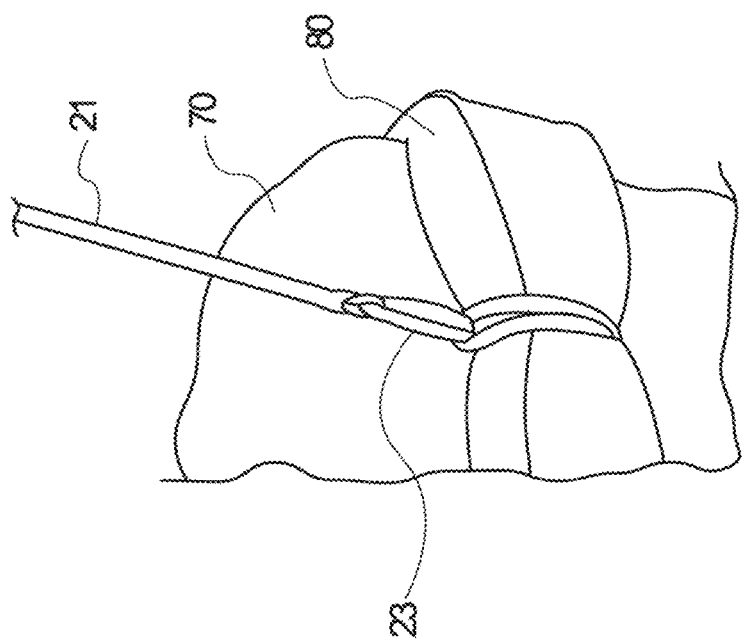
Figure 8F:
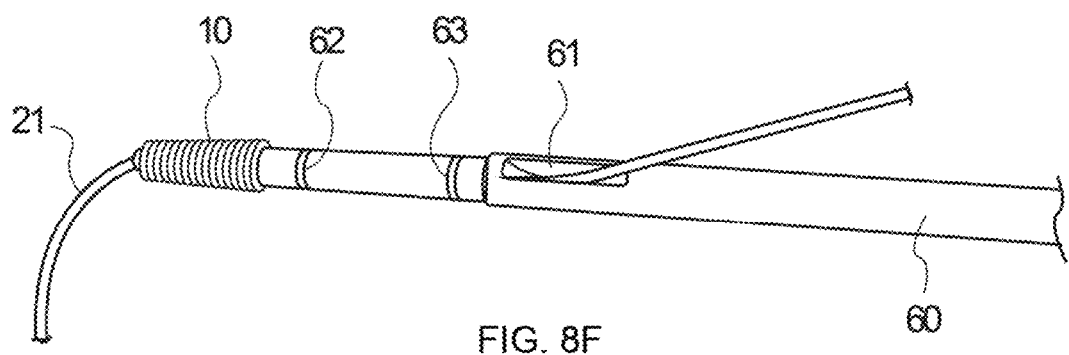

With the filament 20 now positioned on the labrum 80 (FIG. 8A, either around the labrum as shown or through the labrum), the filament may be maneuvered such that both the first and second ends are outside the body of the patient (and the cannulated guide, if present), in the proximal direction, such that the operator may pass the first end 21 through the loop 23 of the second end 22 (FIG. 8B). Of course, if this can be accomplished at the surgical site without trouble, this step may alternatively be performed at the surgical site or even within the cannlated guide (if present). The first end 21, once through loop 23, may then be pulled such that loop 23 travels along the length of the filament and to the labrum tissue 80 (FIGS. 8C-D). The filament is now secured to the tissue in a "luggage tag"—type configuration (FIG. 8D). It should be noted that either the preparation of the bone hole 75 (FIG. 8E) or the passing and positioning of the filament 20 onto the labrum 80 (FIGS. 8A-D) may be completed first, followed by the other.

Figure 8G:
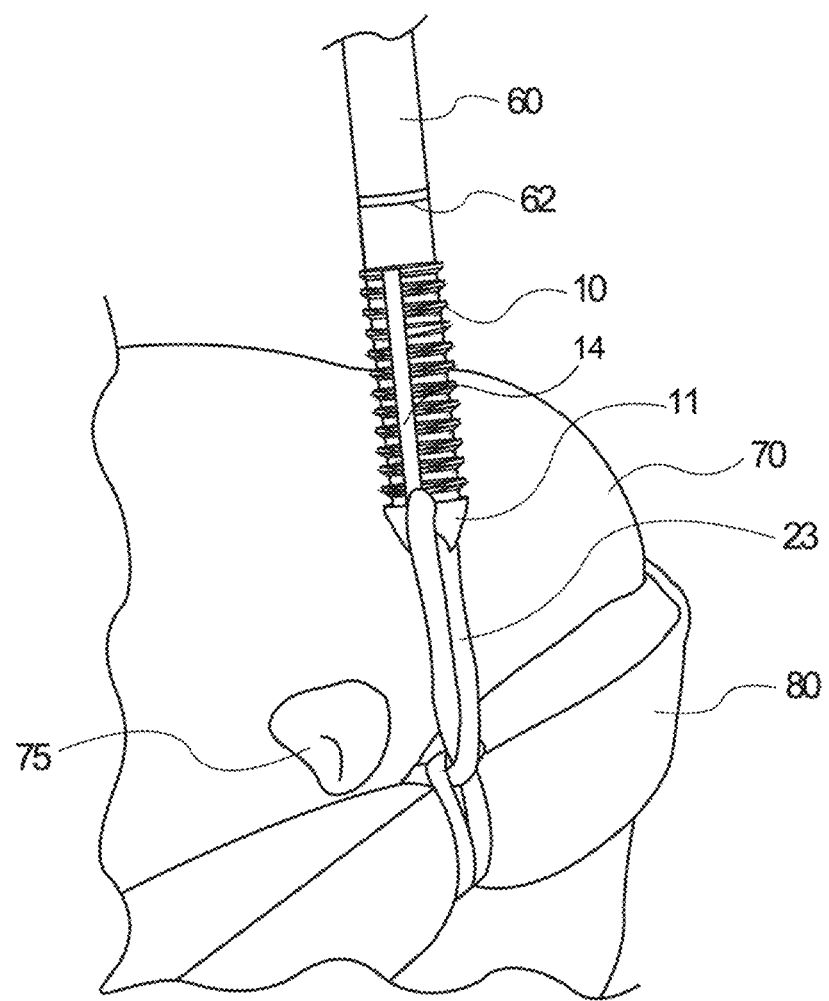

The first end 21 of filament 20 may be placed within the cannulated body of the anchor 10, which is engaged with an inserter 60 (FIG. 8F), and the anchor may travel along the filament towards the second end 22. The inserter 60 may also be cannulated along at least a portion of its length such that the filament may pass through the anchor 10, out the proximal end of anchor 10 and into the cannulated portion of the inserter. The filament may then pass completely through the inserter, if the entire length of the body is cannulated, or the filament may exit through an opening 61 in the side of the inserter, if only a portion of the inserter is cannulated (as in FIG. 8F). The first end 21 may have increased stiffness to allow for ease of threading the anchor and inserter onto the filament. In one example, the stiffened portion of the filament 21 may have a length sufficient to span the distance between the distal end 11 of the anchor to the exit opening 61 through the side of the inserter, which may provide for simplified threading of the filament through the anchor and inserter. The anchor, such as anchor 10 of FIGS. 1-3, engaged with inserter 60 (FIG. 8F), may now be moved towards the surgical site (FIG. 8G). If used at all, the cannulated guide may be removed from the surgical site prior to the step of moving the anchor into the surgical site (though as above, it may be removed prior to passing the filament, if drilling the bore hole is performed prior to passing the filament), however, in some embodiments, the anchor 10 and inserter 60 may pass through the cannulated guide and to the surgical site.

Once the anchor is at the surgical site, the distal end 11 of the anchor engages the filament (FIG. 8G). For example, at least one of the tips 12a, 12b may pierce the filament, such as at the intersection of the loop 23 with the rest of the filament, to engage the filament. Alternatively, the distal end 11 may be maneuvered, using the inserter 60, such that a portion of the filament, such as the loop 23, is engaged by the saddle 13 (as in FIG. 8G). In any event, once the distal end 11 engages the filament, a portion of the loop 23 may be positioned within the saddle 13 and another portion of the loop may be positioned within a portion of the groove 14 (FIGS. 8H-I).

Figure 8H:
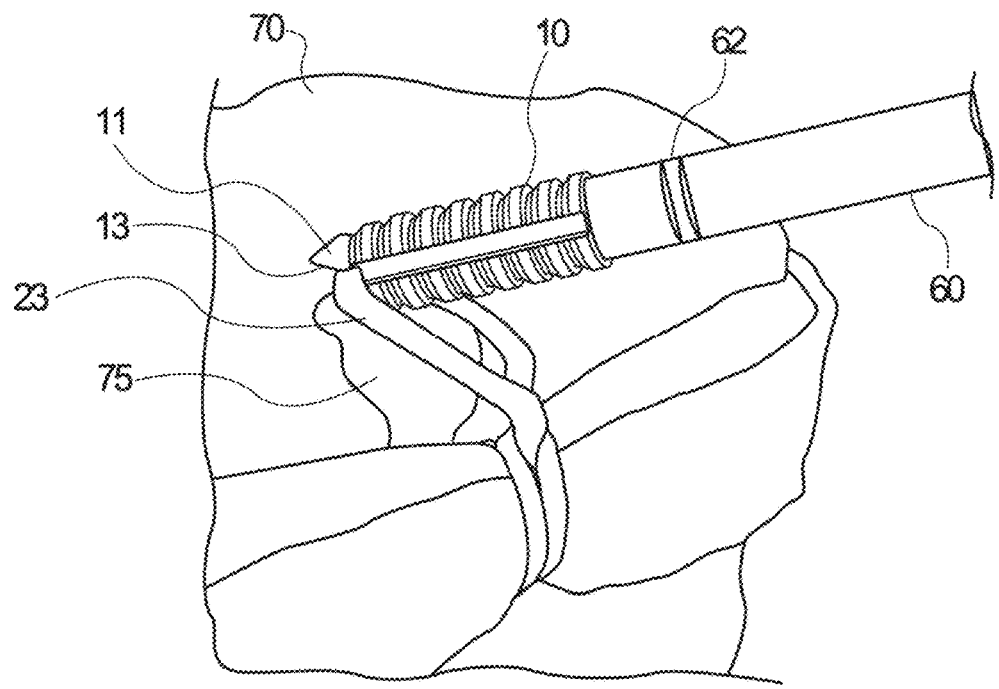
Figure 8I:
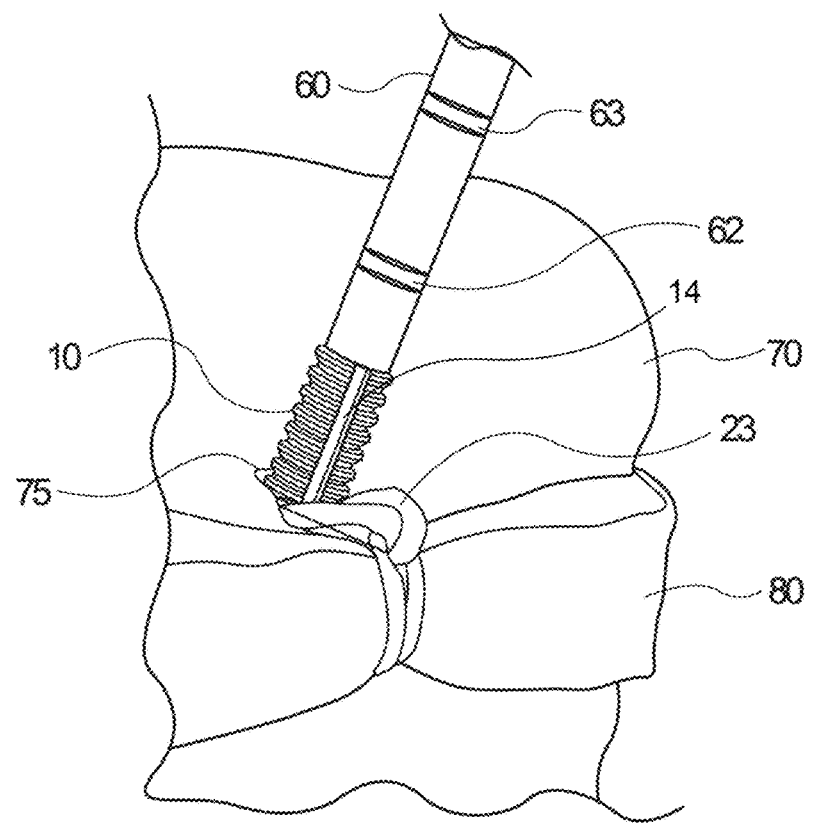

The distal end 11 of the anchor is then directed to the bone hole 75, thereby drawing the filament 20, and secured tissue 80, to the bone hole as well (FIGS. 8H-I). Such drawing of the tissue may also tension the tissue. The distal end 11 of the anchor is then placed within the bone hole 75, and specifically within the second portion of the bone hole, as the second portion has a sufficient diameter to accommodate the anchor (FIG. 8I). At this position, the distal end 11 of the anchor is engaged with the wall of the bone hole 75 and is positioned against the bottom surface of the second portion of the bone hole (at which point the bone hole steps down to the first portion having the first diameter), though the remainder of the anchor is still protruding from the bone surface. Moreover, in this position, the tissue anchor, while engaged with the wall of the bone hole, may still have a weak pull-out strength such that it may be easily removed from the bone hole, if needed, for reinsertion or repositioning.

Figure 8J:
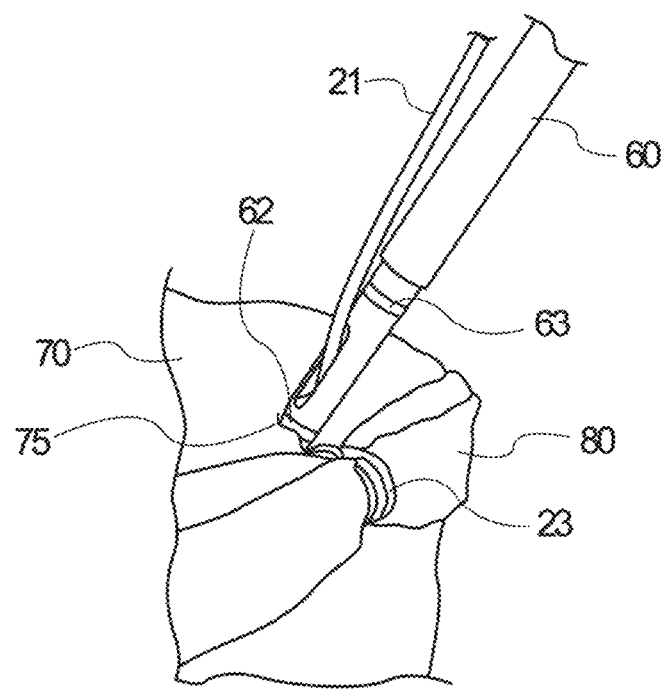
Figure 8K:
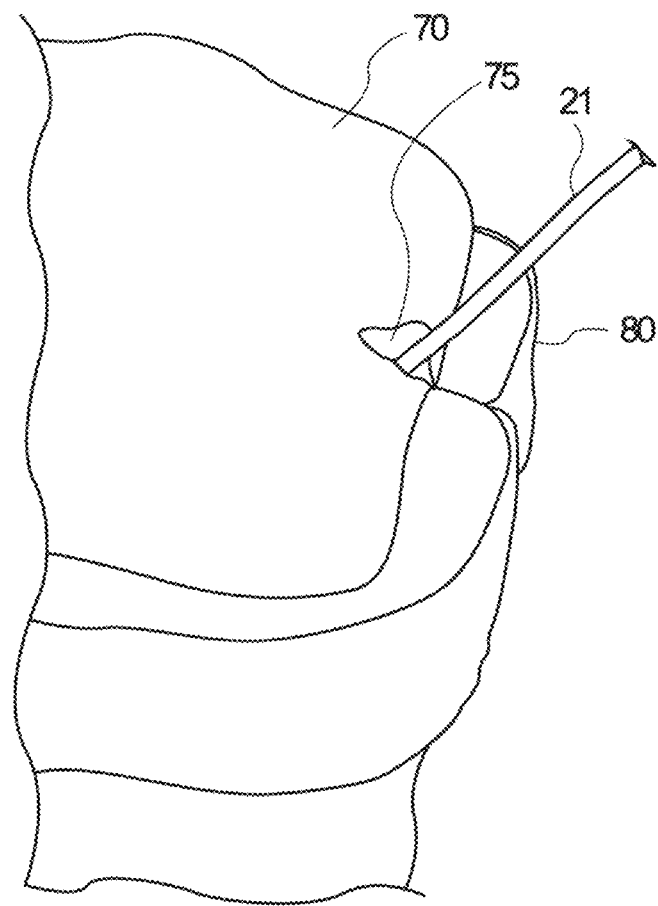

Once in this position, the operator may, using a rubber mallet or the like, apply a force to the inserter 60 which forces the anchor further into the bone (FIG. 8J). As the anchor drives distally, into the first portion of the bone hole (the pilot hole), the anchor bores through the cancellous bone, thereby forming a bone hole having the same diameter as the anchor along the length of the already-formed pilot hole. Further, based on the above exemplary dimensions, the distal tip of the anchor may extend beyond the end of the first portion of the bone hole and deeper into the cancellous bone, such that the anchor is completely self-tapping into the cancellous bone. The operator continues applying such a force to the anchor until the proximal end 16 of the anchor is flush with, or below, the surface of the bone (FIG. 8K). For example, the inserter may have a first laser mark 62 indicating that, once flush with the outer cortical bone surface, the anchor 10 is sufficiently deep within the bone, though at a minimum range of such depth. The inserter 60 may also include a second laser mark 63 indicating that, once flush with the outer cortical bone surface, the anchor 10 is at a depth towards the maximum range of sufficient depth. Thus, the operator may force the anchor 10 to a depth at one of the two laser marks 62, 63 or at a position between the two laser marks 62, 63 on the inserter 60. The operator may position the anchor 10 at a certain depth dependent upon various factors, including bone quality, surrounding anatomy, and the like. Furthermore, the operator may position the anchor at a particular depth to obtain a desired tension on the tissue 80 being secured. For example, if at the first laser mark 62 the tissue is still too loose, the operator may drive the anchor 10 deeper into the bone 70, towards a depth denoted by the second laser mark 63, and by doing so, the operator may be increasing tension on the tissue 80. Thus, the depth of the anchor 10 may be adjusted to attain a desired tension on the tissue 80 being secured, which may result in a better repair.

At this position, the anchor is thereby secured within the bone hole due to the ridge or ridges 15 on the outer surface of the anchor which assist in preventing back-out of the anchor from the bone hole. The surrounding cancellous bone, following the boring by the anchor, may, due to its inherent elasticity, interdigitate with the ridges, whereby the cancellous bone may gravitate towards the anchor such that cancellous bone fits against the surface of the anchor, in between and around the ridges.

Figure 8L:
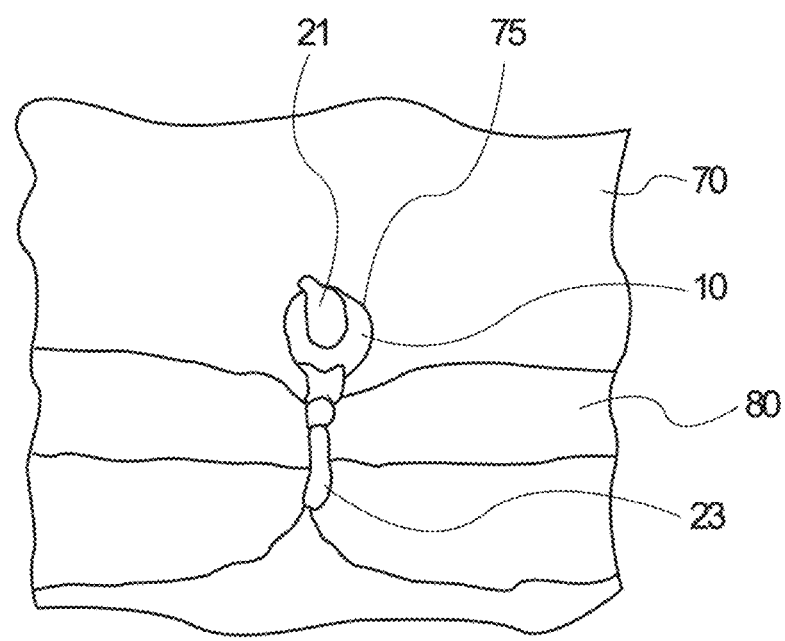

The anchor is now secured within the bone hole, thereby also securing the filament in place. The loop 23 of the filament 20 remains engaged with the distal end 11 of the anchor 10, while the remaining portion of the loop may be positioned within the groove 14 and out of the bone hole, where it remains engaged with the tissue, which is now positioned at or adjacent to the bone hole (FIGS. 8K-L). The remaining portion of the filament, extending to the first end 21, extends from the distal end 11 of the anchor 10, at the intersection with loop 23, through the cannulated body of the anchor 10, and out of the surgical site. This length of filament may be cut (typically where the filament exits from the proximal end 16 of the anchor 10) and removed from the surgical site (FIG. 8L), and the cannulated guide is withdrawn and the wound is closed as is known in the art.

It should be noted that the cannulated guide is optional for this method. As seen in the illustrations of FIG. 8, the cannulated guide is not present, but instead, the inserter 60 merely passes through a common surgical cannula (not shown) and directly to the surgical site. Thus, this method may be performed entirely without a cannulated guide. In another alternative, a cannulated guide, such as a drill guide, may be used with the drill to prepare the bone hole, but is then removed, along with the drill, once the bone hole 75 has been prepared. As mentioned above, the preparation of the bone hole may occur prior to or subsequent to the passing of the filament around or through the tissue 80.

Alternatively, instead of cutting the remainder of the filament 20, once the anchor is positioned in bone, this length of filament may be maneuvered to a second anchor, additional tissue, or the like, to be used in further securement of soft tissue as is required. For example, in an alternative embodiment, a method for the repair of a tissue, such as a rotator cuff, may proceed largely as described above. However, once the anchor is secured in bone (as in FIG. 8K), at a medial position (such that the tissue may drape over the location of the bone hole 75), rather than cutting the remaining portion of the filament 20, this portion is instead passed through the tissue, and passed over the tissue in a lateral direction, to a second bone hole positioned lateral to the reattachment footprint of the rotator cuff tissue. Once in this position, a second anchor, such as a ReelX STT suture anchor (Stryker Endoscopy, San Jose, Calif.), may be positioned on the filament and may be used to secure the resulting suture bridge extending from the first anchor to the second anchor.

The present invention also includes various alternative embodiments of methods for tissue repair utilizing the above-discussed devices. In some embodiments, the filament 20, 120 may be used on its own, without anchor 10, or with another type of anchor, such as the above ReelX STT anchor (as in FIGS. 9A-C, below). As above, such alternative methods may be performed without a cannulated guide, or the method may include the use of a cannulated guide for drilling the bone hole, or additionally for other steps. Such methods may also utilize a single filament 20, 120 or multiple filaments 20, 120, in conjunction with one or more anchors of various type.

In one alternative embodiment for tissue repair, such as the repair of a torn rotator cuff, for example, a first filament 20 may be secured to the cuff at a first location using the "luggage tag" configuration. The first end 21 of the filament may then be tensioned laterally to pull the tissue towards a first bone hole prepared laterally to the footprint of the rotator cuff tissue. The filament first end 21 may then be engaged by an anchor, such as the ReelX STT anchor, to secure the tissue. Furthermore, this method may include a second filament 20 which may be secured to the cuff at a second location, separate from the first location, using the "luggage tag" configuration. The first end 21 of the second filament may then be tensioned laterally to pull the tissue towards a second bone hole prepared laterally to the footprint of the rotator cuff tissue. The first end 21 of the second filament may then be engaged by an anchor, such as the ReelX STT anchor, to secure the tissue. In an alternative, the first ends of both the first and second filaments may be tensioned laterally to a single bone hole and thereby engaged by a single anchor to secure the tissue.

Figure 9B:
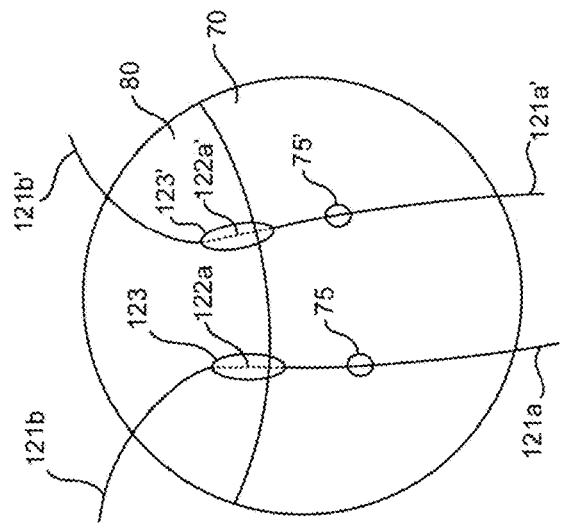
FIGS. 9A-C illustrate various steps of another embodiment of a method of the present invention.
Figure 9C:
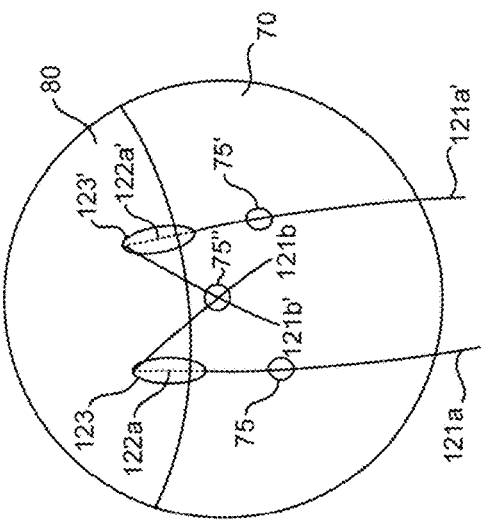
Figure 9A:
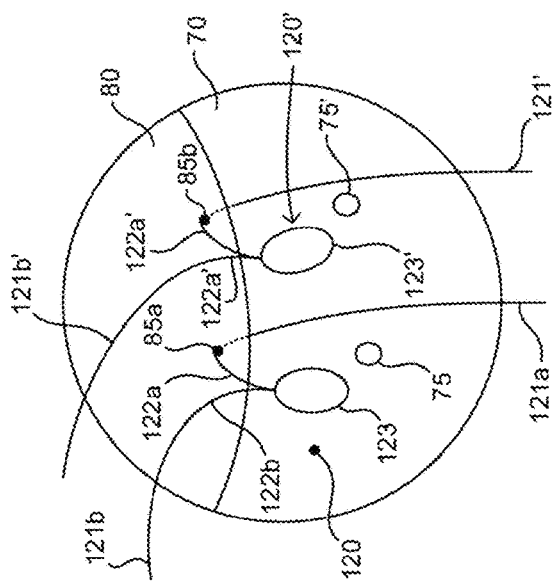

In another embodiment, illustrated in FIGS. 9A-C, two filaments and two separate suture anchors, similar to those described in the previous embodiment, may be used to repair soft tissue, for example, rotator cuff tissue 80. In this embodiment, however, filament 120, each having two discrete lengths of filament, or tails, are used (see FIG. 5). The initial steps of this embodiment are similar to those above. Namely, each filament 120, 120' is passed through the cuff 80 at first and second locations 85*a*, 85*b*, respectively (see FIG. 9A), and secured thereto by passing the first end 121*a*, 121*a*' of the first tail through the loop 123, 123' (see FIG. 9B) to form the luggage tag configuration. At this position, the loop 123, 123' and second end 122*a*, 122*a*' of the first tail wrap around a portion of the cuff tissue such that, effectively, two strands (of each loop) are positioned on the top surface of the tissue, and a single strand (the second end of each first strand) is positioned on the bottom surface of the tissue, and the loop and first strand engage one another both at the edge of the tissue 80 and at the first (or second) location 85*a*. Such contact with the tissue may provide a strong connection between the filament and tissue which may provide for an effective repair (e.g., decreases the risk of the filament tearing the tissue). Of course, a portion of the loop may be positioned on the bottom of the tissue (or conversely, a portion of the second end 122*a* may be positioned on the top of the tissue) depending on the position of the first (or second) location, the size of the loop 123, or the like, though it is preferred that the loop be on the top surface of the tissue and the single strand be on the bottom surface of the tissue.

Once the luggage tag is positioned on the tissue, the first ends 121*a*, 121*a*' are tensioned and positioned adjacent to lateral bone holes 75, 75' in bone 70, respectively, and are each engaged by an anchor, such as the ReelX STT anchor, to secure the tissue. During the tensioning step, the tissue may be drawn laterally toward the bone holes. Of course, in another configuration, the first ends 121*a*, 121*a*' may be crossed such that, for example, first end 121*a* is secured at bone hole 75' and first end 121*a*' is secured at bone hole 75.

Once the first tails (having first ends 121*a*, 121*a*') are secured at bone holes 75, 75', the second tails may then be manipulated by the operator. These tails may be used to secure further tissue, may be secured to one another, or the like. In the illustrated exemplary embodiment (see FIG. 9C), the two second tails are engaged by an anchor, such as the ReelX STT anchor, to secure the tissue at a third bone hole 75". Of course, this bone hole 75" may be positioned anywhere desired. Again, using the illustrated example, the operator may tension the second tails by pulling first ends 121*b*, 121*b*' laterally, towards bone hole 75" to engage a bone anchor and secure the filaments to maintain tension.

As a result, as in FIG. 9C, an effectively double row suture bridge configuration results which provides for a large footprint to maintain the tissue against the bone surface. Additionally, as illustrated, only two lengths of filament (second ends 122*a*, 122*a*') are positioned between the tissue 80 and bone 70, which allows for direct contact between the tissue and bone along substantially the entire surface area of the repair.

In another variation to this embodiment, an anchor 10 may be positioned under tissue 80, and additionally, an anchor may be positioned underneath both first and second positions 85*a*, 85*b*. Anchor 10, at these positions, may engage the loops 123, 123', or either tail at positions 122*a* and/or 122*b*, and 122*a*' and/or 122*b*'. The tails may then be passed over the tissue 80 and to at least one lateral anchor as discussed above. Such variations may provide for additional securement of the soft tissue 80 to the bone 70.

Figure 10B:
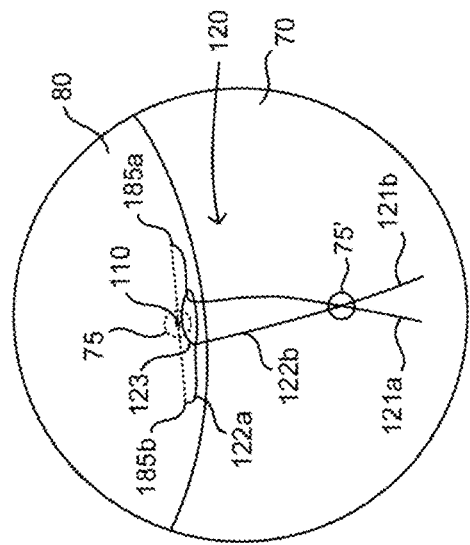
FIGS. 10A and 10B illustrate various steps of another embodiment of a method of the present invention.
Figure 10A:
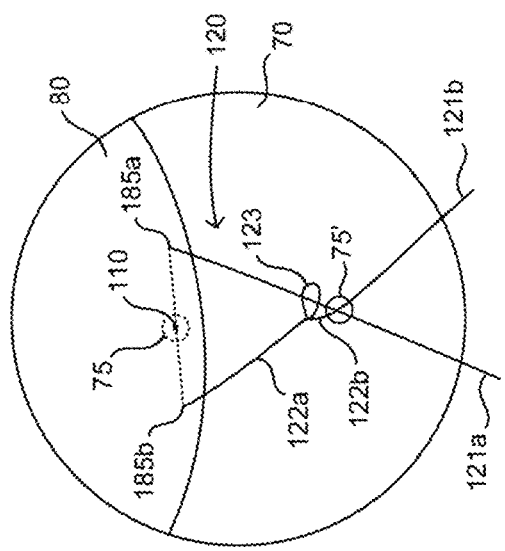

In yet another embodiment, a method of repair of soft tissue may include the use of a filament 120 and a first anchor 110, as illustrated in FIGS. 10A-B. Anchor 110 may be a standard suture anchor as is known in the art. The anchor 110 is positioned in bone 70 under the soft tissue 80, such as a rotator cuff, and one of the tails of filament 120 is engaged by the anchor. For example, the anchor may include an eyelet and the tail of the filament may be passed through the eyelet. The filament tail, such as tail having first end 121*a* in FIG. 10A, which is engaging the anchor, is passed through the tissue at a first location 185*a*, and positioned in a lateral direction relative to the tissue 80. The second tail, including first end 121*b* as in FIG. 10A, is also passed through the tissue at a second location 185*b* and first end 121*b* may be positioned in a lateral direction relative to the tissue. As illustrated in FIG. 10A, as the second tail (ending in first end 121*b*) is passed through the tissue, the loop 123 and the second end 122*a* of the first tail are also pulled through the tissue at location 185*b*. Since the filament freely slides through the eyelet, however, the location of the loop 123 may be adjusted to, for example, be adjacent to either of the first location 185*a*, the second location 185, or any other location the operator may desire.

Once the filament is positioned relative to the tissue, the first end 121*a* may be passed through loop 123 to form a luggage tag configuration between the first location 185*a* and the second location 185*b*, as shown in FIG. 10A. Further manipulation of first ends 121*a*, 121*b* may tension the luggage tag configuration such that loop 123 is pulled adjacent the outer surface of tissue 80, as in FIG. 10B. Once again, the operator may position loop 123 to be adjacent either the first location 185*a* or the second location 185*b*, or alternatively, as in FIG. 10B, the loop 123 may be positioned over anchor 110 such that it is generally equidistant from the first and second locations 185*a*, 185*b*. The position of FIG. 10B may be beneficial to assist the operator in creating an even repair along the length of the tissue 80. With the loop 123 in position against tissue 80, first ends 121*a*, 121*b* may be tensioned further in a lateral direction towards a lateral bone hole 75', and secured at bone hole 75' by a second anchor positioned therein. The tension applied to first and second ends 121*a*, 121*b* may tension the tissue 80 in the lateral direction, as well as cause the loop 123 to migrate laterally. Such lateral tension may return the tissue to a native footprint (as in the example of a rotator cuff repair), or at least create desirable tension on the tissue to form a reliable and beneficial repair.

As with the other method embodiments discussed above, this embodiment may also include variations as to the number of filaments, number of tails on each filament, number of anchors, positioning of anchors, and the like. For example, in one alternative, two medial anchors, positioned under the tissue 80, may be positioned such that a first medial anchor is at the first location 185*a* and a second medial anchor is positioned at the second location 185*b*. The tails (extending to first ends 121*a*, 121*b*), extending from the first and second locations 185*a*, 185*b*, may then extend to a single lateral anchor, as discussed above, or alternatively to two lateral anchors. In the alternative of two lateral anchors, the tails may, following passage through the loop 123, extend in generally parallel fashion relative to one another from the first and second locations 185*a*, 185*b* to first and second lateral anchors, respectively. Alternatively, the first and second tails 121*a*, 121*b* may be crossed such that the tail extending from the first location 185*a* may extend to the second lateral anchor and the tail extending from the second location 185*b* may extend to the first lateral anchor.

Figure 11B:
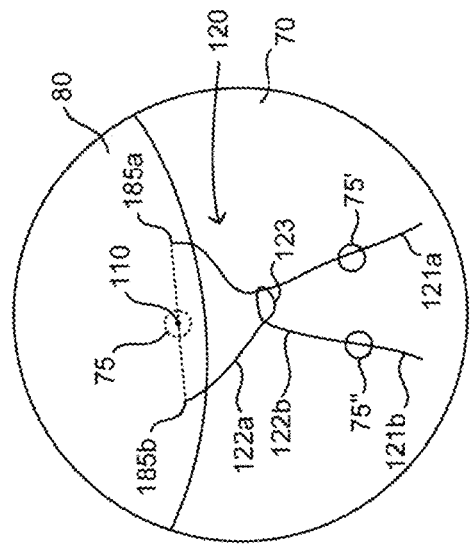
FIGS. 11A and 11B illustrate various steps of another embodiment of a method of the present invention.
Figure 11A:
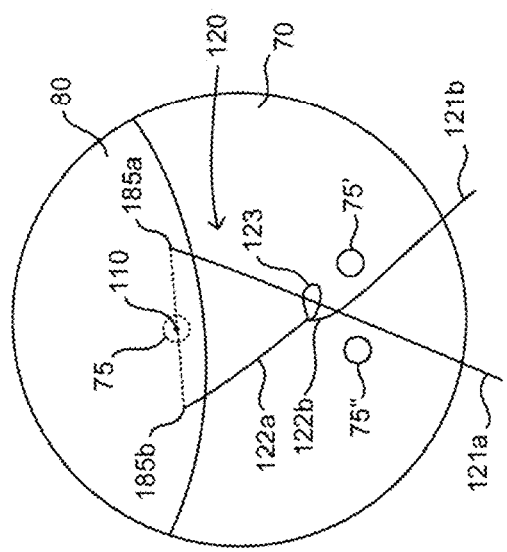

A further exemplary variation is illustrated in FIGS. 11A-B. This embodiment includes a similar configuration as the embodiment of FIGS. 10A-B above, with the exception that this embodiment includes two lateral bone holes 75' and 75". Thus, the initial steps of this illustrative embodiment is identical to that of FIGS. 10A-10B above, except an additional lateral bone hole 75" is prepared. In FIG. 11A, as in FIG. 10A above, the first end 121*a* of the first tail is passed through loop 123 to create the luggage-tag configuration, and both first ends 121*a*, 121*b* of first and second tails are positioned laterally relative to the tissue 80 (in this example, rotator cuff tissue) and towards bone holes 75', 75". As illustrated in FIG. 11B, the tissue repair is made by tensioning first end 121*a* of the first tail in the lateral direction. Such tension may also position the loop 123 laterally (FIG. 11B) as well as tension the tissue 80 laterally, though the filament may be adjusted to position the filament anywhere between, effectively, the second location 185B and the bone hole 75'. The operator may then tension first end 121*a* (while maintaining an amount of tension on the second tail, through first end 121*b*, to maintain the positioning of the loop 123) to tension the luggage tag configuration and create tension on the tissue 80 as desired. The operator may then secure the first tail in bone holes 75' using a suture anchor to secure the repair. Once the first tail is secured at bone hole 75', the second tail, having first end 121*b*, may then be secured at bone hole 75". When securing the second tail, the operator may place any desired tension on the second tail, such that the second tail may tension the loop, and pull it towards the second bone hole 75", and may also impart additional tension on the tissue 80. Alternatively, the tension on the first tail may be only a moderate amount, sufficient to create a stable construct, and then the operator may use the second tail to impart the tension on the loop 123, and thus the first tail and the tissue, to create a reliable and beneficial repair.

In any of such methods using the devices of the present invention, the use of filament 20, 120 provides for a stronger and more reliable repair of the soft tissue due to the absence of a knot along its length. The loops 23, 123 of such filaments are a woven portion of the filament, and thus a knot is not required, thereby eliminating a weak point in the length of the filament commonly found in other filament arrangements utilizing a knot. Additionally, in those embodiments in which the loop and a portion of a tail are wrapped around the tissue in a "luggage tag" configuration, such a configuration provides for a stronger and more stable connection between the filament and the tissue than a simple pass-through of the suture, or a knot. Such a configuration, additionally, may decrease the likelihood of the tissue tearing, or other trauma, at the location of the suture passing through the tissue.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A surgical drill, comprising:
a shaft extending along a longitudinal axis and having a boring structure at a distal end of the shaft; and
a concentric element positioned along the shaft proximal to the boring structure, the concentric element having a distal face at a distal end of the concentric element, at least a portion of the distal face extending radially outwardly from the longitudinal axis farther than a radially outermost portion of the boring structure, the distal face of the concentric element including a marking material positioned thereon, and the distal face of the concentric element oriented such that the distal face is configured to contact a bone and, thereby, mark a surface of the bone with the marking material during advancement of the drill to form a hole in the bone by the boring structure.

2. The drill of claim 1, wherein the concentric element is rotatable independently of the shaft, such that rotation of the concentric element with respect to the shaft does not advance a longitudinal position of the concentric element along the longitudinal axis of the shaft.

3. The drill of claim 1, wherein the drill is configured such that contact between the distal face of the concentric element and the bone prevents further advancement of the drill into the bone, thereby limiting a depth of the hole in the bone formed by the drill to a distance between a distal-most portion of the boring structure and the distal face of the concentric element.

4. The drill of claim 1, wherein the boring structure has a first portion and a second portion, the second portion being positioned proximal to the first portion, wherein the first portion has a first diameter and the second portion has a second diameter, the second diameter being larger than the first diameter such that a step is defined between the first and second portions.

5. The drill of claim 4, wherein the first portion of the boring structure includes at least one flute, and wherein the second portion of the boring structure includes another at least one flute.

6. The drill of claim 1, wherein the shaft has a groove formed in an outer surface of the shaft, the concentric element being positioned within the groove.

7. The drill of claim 6, wherein the groove engages the concentric element to prevent movement of the concentric element along a longitudinal dimension of the shaft.

8. The drill of claim 1, wherein the shaft includes a flexible portion.

9. A system for securing tissue to bone, comprising:
the drill of claim 8; and
a curved guide adapted to receive the drill therein.

10. A system for securing tissue to bone, comprising:
the drill of claim 1; and
a guide adapted to receive the drill therein, wherein an outer surface of the concentric element is adapted to contact an inner surface of the guide to maintain the drill in a centered position within the guide.

11. A system for securing tissue to bone, comprising:
the drill of claim 1; and
an anchor for securing tissue to bone.

12. The system of claim 11, wherein the anchor comprises a body adapted to be inserted into the hole in the bone formed by the drill, the body having a distal end and a proximal end, wherein the distal end of the body includes a saddle defining a distally oriented concavity open at the distal end of the body, the saddle being adapted for engaging a loop of a filament by moving the body towards the loop from a position remote from the loop until the loop is received within the saddle, wherein the body includes a cannulation extending longitudinally between the distal end and the proximal end of the body, the cannulation communicating with the saddle, and wherein the body has a first groove extending longitudinally along an exterior surface of the body, the first groove extending proximally from the saddle such that a distal end of the first groove communicates with a proximal end of the concavity defined by the saddle.

13. The system of claim 11, further including a filament having a first end and a second end, the second end including a loop.

14. The system of claim 13, wherein the loop of the filament is formed without a knot by portions of the filament woven together.

15. The system of claim 11, further including an inserter instrument adapted to engage the anchor for positioning the anchor within the hole in the bone formed by the drill.

16. The system of claim 15, wherein the inserter instrument includes at least one indicia positioned along the inserter instrument so as to indicate either a minimum depth or a maximum depth of insertion of the anchor into the hole in the bone formed by the drill.

17. A method for drilling a hole in bone, comprising:
rotating the boring structure of the drill of claim 1 about the longitudinal axis of the shaft; and
advancing the shaft of the drill into the hole in the bone formed by the boring structure until the distal face of the concentric element contacts the bone.

18. The method of claim 17, further comprising applying a mark to a surface of the bone with the marking material positioned on the distal face of the concentric element.

19. The method of claim 17, further comprising forming the hole in the bone with the boring structure such that the hole has a first portion having a first diameter and a second portion having a second diameter, the first diameter being smaller than the second diameter such that a step is defined between the first and second portions of the hole.

* * * * *